US012569527B2

(12) United States Patent
Unamunzaga Escosura et al.

(10) Patent No.: US 12,569,527 B2
(45) Date of Patent: Mar. 10, 2026

(54) *Tetraselmis chuii (T. chuii)* FOR THE TREATMENT OF MALE INFERTILITY

(71) Applicant: FITOPLANCTON MARINO, S.L, El Puerto de Santa Maria (ES)

(72) Inventors: Carlos Unamunzaga Escosura, El Puerto de Santa Maria (ES); Eulalia Mantecón Gálvez, El Puerto de Santa Maria (ES); Carlos Infante Toscano, El Puerto de Santa Maria (ES)

(73) Assignee: FITOPLANCTON MARINO, S.L, El Puerto de Santa Maria (ES)

( * ) Notice: Subject to any disclaimer, the term of this patent is extended or adjusted under 35 U.S.C. 154(b) by 495 days.

(21) Appl. No.: 18/012,808

(22) PCT Filed: Jul. 9, 2021

(86) PCT No.: PCT/EP2021/069117
§ 371 (c)(1),
(2) Date: Dec. 23, 2022

(87) PCT Pub. No.: WO2022/008707
PCT Pub. Date: Jan. 13, 2022

(65) Prior Publication Data
US 2023/0263847 A1 Aug. 24, 2023

(30) Foreign Application Priority Data
Jul. 10, 2020 (EP) .................................... 20382623

(51) Int. Cl.
*A61K 36/05* (2006.01)
*A61P 15/08* (2006.01)

(52) U.S. Cl.
CPC .............. *A61K 36/05* (2013.01); *A61P 15/08* (2018.01)

(58) Field of Classification Search
None
See application file for complete search history.

(56) References Cited

U.S. PATENT DOCUMENTS

| | | |
|---|---|---|
| 2015/0245852 A1 | 9/2015 | Sugihara et al. |
| 2016/0281057 A1 | 9/2016 | Yamashita et al. |
| 2018/0119114 A1* | 5/2018 | Unamunzaga Escosura ............... A61P 39/06 |

FOREIGN PATENT DOCUMENTS

| | | |
|---|---|---|
| EP | 3517175 A1 | 7/2019 |
| JP | 2018518194 | 7/2018 |
| WO | 2014045582 | 3/2014 |
| WO | 2015064109 | 5/2015 |
| WO | 2016177853 | 11/2016 |

OTHER PUBLICATIONS

Pei-Tzu Wang et al., "Oral supplementation of fucoxanthin-rich brown algae extract ameliorates cisplatin-induced testicular damage in hamsters," Biomedicine and Pharmacotherapy, Feb. 25, 2020, vol. 125.

Alireza Sobhani, MD et al., "Antioxidant Effects of Brown Algae Sargassum on Sperm Parameters: Consort-Compliant Article," Medicine, Dec. 1, 2015, vol. 94, No. 52.

K. Subasankari et al., "Screening of Microalgae as a Potential Source of Photoprotective Pigments, " IJSRR, Sep. 2018, pp. 220-231, vol. 7, No. 3.

Ching-Lung Chen et al., "Dewatering and drying methods for microalgae," Drying Technology, Mar. 2015, pp. 143-454, vol. 33.

Bheda, B et al., "Drying of algae by various drying methods," IDS'2018—21st International Drying Symposium, Sep. 11-14, 2018, pp. 1,791-1,797.

S. Vorilhon et al., "Accuracy of human sperm DNA oxidation quantification and threshold determination using an 8-OHdG immunodetection assay," Human Reproduction, Feb. 2018, pp. 553-562, vol. 33, No. 4.

Robert R.L. Guillard et al., "Studies of marine planktonic diatoms. I. Cyclotella nana Hustedt, and Detonula confervacea (cleve) Gran," Can J Microbiol., Apr. 1962, pp. 229-239, vol. 8.

Koji Mikami et al., "Biosynthetic Pathway and Health Benefits of Fucoxanthin, an Algae-Specific Xanthophyll in Brown Seaweeds," Int. J. Mol. Sci., Jul. 2013, pp. 13,763-13,781, vol. 14.

Albert Salas-Huetos et al., "The Effect of Nutrients and Dietary Supplements on Sperm Quality Parameters: A Systematic Review and Meta-Analysis of Randomized Clinical Trials," Adv Nutr., Nov. 2018, pp. 833-848.

Arturo Morales Martinez et al., "A randomized clinical study assessing the effects of the antioxidants, resveratrol or SG1002, a hydrogen sulfide prodrug, on idiopathic oligoasthenozoospermia," Asian Pacific Journal of Reproduction, Jun. 2015, pp. 106-111, vol. 4, No. 2.

Ylenia Duca et al., "Current and emerging medical therapeutic agents for idiopathic male infertility," Expert Opinion On Pharmacotherapy, Nov. 2018, pp. 55-67.

International Search Report and Written Opinion for PCT/EP2021/069117, mailed Aug. 10, 2021.

Notice of Reasons for Refusal dated Jan. 28, 2025 in JP application No. 2023501415.

Luciano Negri et al., Effect of superoxide dismutase supplementation on sperm DNA fragmentation, Archivio Italiano di Urologia e Andrologia Oct. 3, 2017; 89, 3, pp. 212-218 doi: 10.4081/aiua.2017.3.212.

MD Bayejid Hosen, et al., Oxidative stress induced sperm DNA damage, a possible reason for male infertility, Iran J Reprod Med vol. 13. No. 9. pp: 525-532, Sep. 2015; PMID: 26568756; PMCID: PMC4637119.

* cited by examiner

*Primary Examiner* — Susan Hoffman
(74) *Attorney, Agent, or Firm* — Pilloff Passino & Cosenza LLP; Rachel K. Pilloff; Sean A. Passino

(57) ABSTRACT

The present invention refers to a biomass of *T. chuii* and a pharmaceutical composition comprising a biomass of *T. chuii* for use in the treatment of infertility in a male subject. It also refers to a method for increasing the quality of the semen of a male subject having normozoospermia, not having hypospermia and not having a disorder characterized by a high percentage of sperm DNA fragmentation (SDF), that comprises the administration of a biomass of *T. chuii*.

13 Claims, 6 Drawing Sheets

*Tetraselmis chuii (T. chuii)* FOR THE TREATMENT OF MALE INFERTILITY

FIELD OF THE INVENTION

The invention relates to the field of compositions for use in the treatment of male infertility associated to deficiencies in semen, wherein said compositions are obtained from a microalgae.

BACKGROUND OF THE INVENTION

Infertility is diagnosed in 12-15% of sexually active couples. In 50% of said couples, infertility is due to a disorder in the male subject, either alone or in combination with a disorder in the female subject.

The defects causing male infertility can be classified as related to the hypothalamus or to the pituitary gland, the testicles, or defective sperm delivery due to disorders in the penis or related sexual glands. Deficiencies in semen parameters are often observed in infertile man. Therefore, male infertility is often diagnosed upon analysis of semen samples from the male subject.

Semen parameters generally altered in infertile man include the volume of a semen sample, approximate number of total sperm cells, sperm motility or forward progression, percentage of sperm with DNA fragmentation (SDF), number of dead sperm cells in the semen or presence of leukocytes in the semen. Alterations in said parameters are classified within different disorders, such as oligozoospermia (very low sperm count), aspermia (absence of semen), hypospermia (low semen volume), azoospermia (absence of sperm in the semen), teratozoospermia (high morphological defects in the sperm), asthenozoospermia (poor sperm motility), necrozoospermia (high number of dead sperm), leucospermia (presence of a high amount of leukocytes in the semen) and high SDF percentage (high percentage of sperm showing DNA fragmentation).

Treatments of male infertility are generally aimed at treating a specific physiological alteration which is most probably the cause of the disorder. For instance, surgery can be used in cases where male infertility is caused by a blockade in the sperm transport system, such as after a vasectomy. Vasectomy is generally surgically reversed in up to 85 percent of cases, however in many cases, men remain infertile even after a successful intervention. In cases where male infertility is due to low testosterone production, hormone treatment can be administered to restore fertility (Luteinizing hormone, LH, and follicle-stimulating hormone, FSH). However, a long period of treatment is required for sperm production to reach levels associated to male fertility.

Couples where the male subject is diagnosed with male infertility are often advised to follow different assisted reproductive methods. Said invasive methods include intra-uterine insemination (IUI), in vitro fertilization (IVF), or IVF with intracytoplasmic sperm injection (ICSI).

Therefore, there is a need in the art for non-invasive and effective treatments of male infertility, independently of the cause of the disorder.

SUMMARY OF THE INVENTION

The authors of the present invention have observed that the administration of microalgae from the species *Tetraselmis chuii (T. chuii)* to male subjects with disorders associated to male infertility and characterized by an alteration in a specific semen parameter, such as idiopathic oligozoospermia, asthenozoospermia, and/or teratozoospermia, results in the normalization of the corresponding semen parameter and thus contributes to the treatment of the disorder.

In particular, as shown in Examples 1-4 and in FIGS. 1-8, they have observed that the levels of the parameters semen volume, sperm concentration, total sperm number per ejaculate and progressive motility in semen samples of subjects with idiopathic oligozoospermia, asthenozoospermia, and/or teratozoospermia are increased upon administration of *T. chuii*, from levels below the corresponding Lower Reference Limit (LRL) to levels above said LRL. In addition, as shown in example 5 and in FIG. 10, they have observed that after administration of *T. chuii*, the percentage of subjects analyzed showing teratozoospermia diminished from 35% to 10%, indicating that the percentage of morphologically normal spermatozoa in the semen samples of said patients increased to a value above the corresponding LRL. Finally, as shown in example 6 and in FIG. 11, the authors of the present invention have observed that after administration of *T. chuii*, 30% of patients originally diagnosed with idiopathic oligozoospermia, asthenozoospermia, and/or teratozoospermia have normozoospermia.

Thus, in a first aspect, the invention relates to a biomass of *T. chuii* or a pharmaceutical composition comprising the biomass of *T. chuii* for use in the treatment of infertility in a male patient.

In a second aspect, the invention relates to a method for increasing the quality of the semen of a male subject having normozoospermia, not having hypospermia, and not having a disorder characterized by a percentage of Sperm DNA Fragmentation (SDF) above a reference value, comprising treating the subject by administering a biomass of *T. chuii*.

In a third aspect, the invention relates to a use of a biomass of *T. chuii* as an oral supplement for increasing the quality of the semen of a male subject having normozoospermia, not having hypospermia, and not having a disorder characterized by a percentage of SDF above a reference value.

DETAILED DESCRIPTION OF THE INVENTION

I—Medical Use of the Invention

Figure 1:
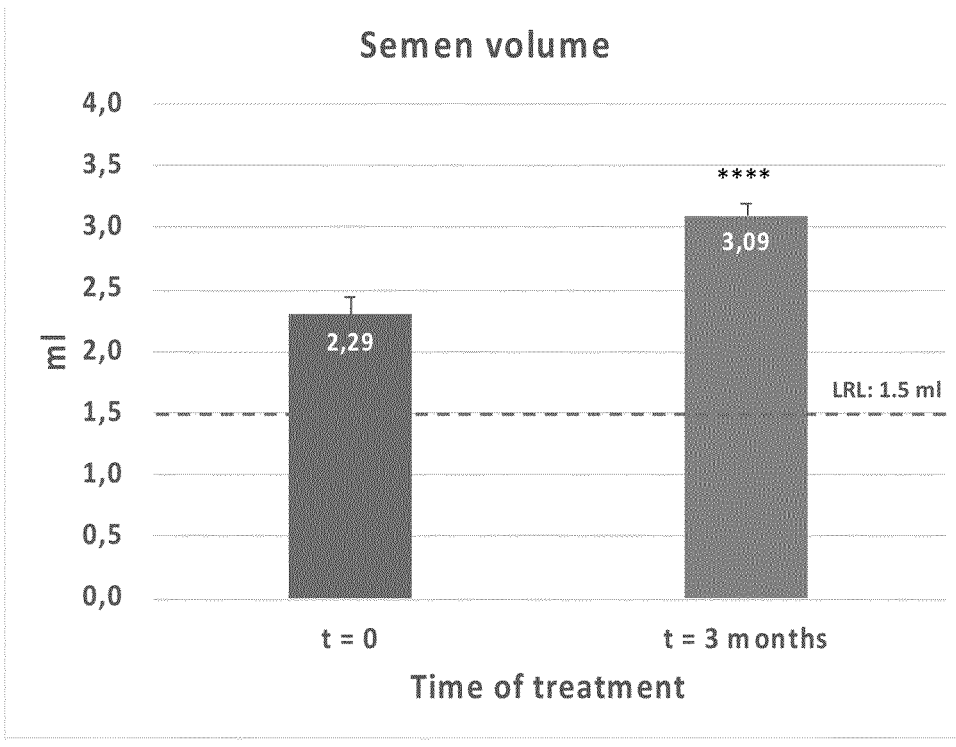
FIG. 1 shows mean values (+SEM) of the parameter semen volume (VOL) just at the commencement of the trial and after 3 months of supplementation with *T. chuii*. The dashed line indicates the Lower Reference Limit (LRL) stablished by the World Health Organization (WHO), in the "WHO laboratory manual for the Examination and processing of human semen" (Fifth edition, 2010). ****: $p<0.0001$.

In a first aspect, the invention relates to a biomass of *Tetraselmis chuii* (*T. chuii*), a protein extract of *T. chuii* or a pharmaceutical composition comprising the biomass of *T. chuii* or the protein extract of *T. chuii* for use in the treatment of infertility in a male patient.

The term "*Tetraselmis chuii*", more commonly spelled "*Tetraselmis chuii*" or "*T. chuii*" as used herein, refers to a marine unicellular alga (microalga) belonging to the Chlorodendrophyceae class, Chlorodendrales order, Chlorodendraceae family; which is green, motile and usually grows 10 μm long×14 μm wide. In a particular embodiment, *T. chuii* corresponds to the organism identified in the NCBI database by the Taxonomy ID: 63592 (NCBI:txid63592).

The term "biomass", as used herein, refers to biological material comprising living or recently living organisms. By extension, the term includes not only the biological material or organic matter that constitutes an organism, but also the biological material or organic matter generated in a biological process, spontaneous or not spontaneous (i.e., provoked).

As understood by a skilled person, a biomass of *T. chuii* is a biomass as just defined, wherein the organism is the algae *T. chuii*. Generally, said biomass is obtained from a sample of *T. chuii*.

In a particular embodiment, the biomass of *T. chuii* is obtained from one cell of *T. chuii*. In another particular embodiment, the biomass of *T. chuii* is obtained from several cells of *T. chuii*. Thus, in a preferred embodiment, the biomass of *T. chuii* is obtained from a cell culture of *T. chuii*.

In a particular embodiment, the cell culture of *T. chuii* from which the biomass of *T. chuii* is obtained is performed under suitable conditions for the growth of the microalgae *T. chuii*, well known by an expert in the field. Said conditions are characterized by the use of a suitable medium, such as, for example, F/2 culture medium [Guilard R. R. L. & Ryther, J. H. 1962. "Studies of marine planktonic diatoms. I. Cyclotela nana Hustedt and Detonula confervaceae (Cleve) Gran." Can. J. Microbiol. 8, 229-239], and performance under solar or proper lighting conditions (light intensity) and controlled conditions of pH, temperature and feed carbon dioxide ($CO_2$), as it is well-known for the skilled person in the art. The F/2 culture medium comprises a source of nitrogen, a source of phosphorus, trace elements such as, for example, sodium, iron, copper, zinc, cobalt, manganese and molybdenum as well as a mix of vitamins such, for example, cyanocobalamin (vitamin B12), thiamine (vitamin B1) and biotin in an aqueous medium.

Light intensity is regulated so that photosynthesis is allowed; thus, although it can vary within a broad range, in a particular embodiment, light intensity applied to the culture medium is comprised between 1 and 2000 μmol fotons $m^{-2}$ $s^{-1}$ of photosynthetically active radiation (PAR) in outdoor conditions, indoor typically about 150 μmol fotons $m^{-2}$ $s^{-1}$. pH can vary usually between about 7 and about 8.5, typically about 7.5.

A temperature promoting the growth of *T. chuii* is selected usually comprised between about 17° C. and about 28° C., typically between about 24° C. and 26° C.

Culture is performed with or without aeration, typically with aeration, for example, with approximately 0.5 to 5, preferably about 1-2% $CO_2$ in atmospheric air.

In a preferred embodiment, said culture of *T. chuii* is performed under standard conditions, performed with an F/2 culture medium at 150 μmol fotons $m^{-2}$ $s^{-1}$ (PAR), at a temperature between 24° C. and 26° C., preferably at 25° C., at pH 7.5, and with 1-2% $CO_2$ enriched atmospheric air.

In a further preferred embodiment, the cell culture of *T. chuii* from the biomass of *T. chuii* is performed with F/2 culture medium, in outdoor tubular photobioreactors, under natural photoperiod, at ambient temperature and under pH controlled with $CO_2$ injection. Specifically, said cell culture was performed with F/2 culture medium, with a light intensity between 1-2000 μmol fotons $m^{-2}$ $s^{-1}$ (PAR), at a temperature between 10-35° C., at pH between 7-8.5 and at salinity of 35 practical salinity units (PSU). In addition, it was performed with a photoperiod 12:12 (i.e. 12 hours of light and 12 hours of darkness).

In another particular embodiment, the cell culture of *T. chuii* from which the biomass of *T. chuii* is obtained, is performed under abiotic stress conditions.

As used herein, the expression "abiotic stress" relates to the negative impact of non-living factors on the living organisms in a specific environment. The non-living variable must influence the environment beyond its normal range of variation to adversely affect the population performance or individual physiology of the organism in a significant way.

There are several abiotic stress factors that can affect the growth of microalgae, e.g., *T. chuii*, and the production of compounds and metabolites thereof. However, in a particular embodiment, the abiotic stress applied to the cell culture from which the biomass of *T. chuii* of the medical use of the invention is obtained, is selected from the group consisting of high redox potential, high temperature, high salinity and nitrogen starvation.

According to the invention, an abiotic stress based on a high redox potential comprises maintaining the culture medium with a redox potential of at least 100 mV, at least 200 mV, at least 300 mV, at least 400 mV, at least 500 mV, at least 600 mV, at least 700 mV, at least 800 mV at least 900 mV, at least 1000 mV; said abiotic stress can be obtained by conventional methods for obtaining high redox potential conditions in culture media, such as, for example, by the addition of ozone which is normally generated using an ozone generator by reaction of the air with UV. The amount of ozone to be added is the necessary to achieve and maintain the culture medium with a redox potential of at least 100 mV, at least 200 mV, at least 300 mV, at least 400 mV, at least 500 mV, at least 600 mV, at least 700 mV, at least 800 mV at least 900 mV, at least 1000 mV.

An abiotic stress based on high temperature, according to the invention, comprises maintaining the culture medium at a temperature of at least 28° C., at least 30° C., at least 35° C., at least 40° C., at least 45° C., at least 50° C.; said temperature in the culture medium can be obtained by conventional methods. Since the culture can be indoor or outdoor, for indoor cultures, the temperature of the culturing room must be set above 28° C.; whereas for outdoor cultures, the culture should be done in appropriate locations wherein said temperature is reached naturally by the environmental temperature, for example during Spring and Summer in Southern Spain, e.g., Cádiz, Málaga, Sevilla, etc.

According to the invention, an abiotic stress based on a high salinity condition comprises maintaining the culture medium with a salinity of at least 35 PSU (practical salinity units), at least 40 PSU, at least 45 PSU, at least 50 PSU, at least 100, at least 200, at least 300. The skilled person knows how to determine the salinity of the culture medium by using standard techniques (UNESCO, 1981, "Background papers and supporting data on the practical salinity scale 1978" Unesco Technical papers in marine science, 37). An abiotic stress based on high salinity condition can be obtained easily by adding salts to said culture medium until said salinity condition is reached, for example, by evaporating natural seawater until the target salinity is reached or by adding commercially available sea salts.

An abiotic stress based on nitrogen starvation, according to the invention, comprises growing *T. chuii* under conditions of nitrogen deficiency, limitation or privation; said abiotic stress can be achieved easily by stopping the supply of nitrogen to the culture medium (i.e., by refraining from adding nitrogen to the culture medium).

In a preferred embodiment, the abiotic stress comprises nitrogen starvation. The term "nitrogen starvation", as used herein, refers to a condition in which the supply of nitrogen is such that the nitrate concentration in the culture medium is less than 200 µM. less than 100 µM, less than 10 µM, less than 0.1 µM, less than 0,001 µM.

Methods to obtain the biomass of *T. chuii* are well known by a skilled person in the art. Non-limiting examples of said methods include filtration or centrifugation of a cell culture, or a group of *T. chuii* cells from which the biomass is obtained. Then, the collected biomass is preferably and advantageously washed to remove non-biological material (e.g., mineral salt precipitates and the like).

In a preferred embodiment, the biomass referred in the first aspect of the invention or comprised in the pharmaceutical composition referred in said aspect of the invention is fresh or dehydrated. In another preferred embodiment, said biomass is dehydrated. In a certain embodiment, said biomass is fresh.

The expression "dehydrated biomass" or "lyophilized biomass" as used herein, refers to biomass as defined herein, wherein the water has been completely or partially removed. In a preferred embodiment, the water has been removed completely. In another particular embodiment, the water content removed, corresponds to at least 40%, at least 50%, at least 55%, at least 60%, at least 65%, at least 70%, at least 75%, at least 80%, at least 85%, at least 88.5%, at least 90%, at least 91%, at least 92%, at least 93%, at least 94%, at least 95%, at least 96%, at least 97%, at least 98%, at least 99%, at least 99.5%, preferably to at least 70%, more preferably at least 75% of the weight of the fresh biomass. Methods to determine the percentage of water removed in a dehydrated biomass are well-known by a person skilled in the art, and comprise determining the weight of the given biomass before and after dehydrating said biomass, wherein the difference is the weight of the amount water removed during dehydration. Methods to dehydrate a biomass are also well-known by a person skilled in the art and include solar drying, convective drying, spray drying, freeze drying, roller/drum drying, fluidized-bed drying, vacuum tray drying, and or solar conduction drying (Chen et al., 2015. Dewatering and drying methods for microalgae. Drying Technology 33(4): 443-454; Bheda et al., 2018. Drying of algae by various drying methods. IDS'2018—21st International Drying Symposium, pp 1791-1797. València, Spain, 11-14 Sep. 2018, Editorial Universitat Politécnica de València).

The expression "fresh biomass" as used herein, refers to the biomass which has not been dehydrated, i.e. a biomass wherein the water comprised in the biomass has not been partially or completely removed. In a preferred embodiment, a fresh biomass is that directly obtained by any of the methods provided above to obtain a biomass.

The expression "protein extract of *T. chuii*" as used herein, refers to a sample of proteins obtained upon extraction of proteins from *T. chuii* cells. More specifically, the protein extract is obtained from a sample of *T. chuii*. In a preferred embodiment, the sample of *T. chuii* from which the protein extract is obtained is as the sample of *T. chuii* from which the biomass of *T. chuii* is obtained, and that is defined in any of the embodiments above. Accordingly, the cell culture from which the sample of *T. chuii* from which the protein extract of *T. chuii* is obtained is also as that from which the sample to obtain the biomass of *T. chuii* is obtained. Thus, the cell culture of *T. chuii* from which the sample of *T. chuii* from which the protein extract of *T. chuii* is obtained is as the cell culture defined in any of the embodiments above. i.e. the conditions of said cell culture are any of those defined above.

Methods used to obtain a protein extract of *T. chuii* from a sample of *T. chuii* are well known by an expert in the field. Non-limiting examples of said methods include the addition of an extraction buffer to the biomass of *T. chuii* obtained as described above, followed by a lysis of the cells, the centrifugation of the sample and the isolation of the supernatant of the centrifuged sample. Protein extraction buffers are well known by an expert in the field. A non-limiting example of a protein extraction buffer includes a phosphate buffer such as a 220 mM $KH_2PO_4$ buffer at pH 7.8. Methods to lyse a cell are well-known by an expert in the field and include the use of ultrasounds in several time intervals, such as 4 cycles of ultrasounds at 20% amplification during of 30 sec each, with an interruption of 10 seconds between each cycle. Other non-limiting examples of methods to obtain a protein extract from a sample of *T. chuii* are described in Bleakley S. and Hayes M. 2017. Foods 6(5):33.

The term "pharmaceutical composition", as used herein, refers to a composition comprising a therapeutically effective amount of the biomass of *T. chuii* or of the protein extract of *T. chuii* and at least one pharmaceutically acceptable excipient.

Pharmaceutical compositions according to the invention can be prepared, for instance, as injectables such as liquid solutions, suspensions, and emulsions. The terms "pharmaceutically acceptable excipient", or "pharmaceutically acceptable carrier," "pharmaceutically acceptable diluent", or "pharmaceutically acceptable vehicle" are used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed, and is compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants that enhance the effectiveness of the formulation. Adjuvants could be selected from the group consisting of sterile liquids, such as water and oils, including those of petroleum, animal, vegetable, or synthetic origin, such as peanut oil, soybean oil, mineral oil, sesame oil, and the like. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21st Edition, 2005.

The term "therapeutically effective amount", as used herein, in relation to the biomass or protein extract of *T. chuii*, relates to the sufficient amount of said biomass or protein extract to provide the desired effect, i.e. to achieve an appreciable prevention, cure, delay, reduction of severity or amelioration of one or more symptoms derived from a disease, and will generally be determined by, among other causes, the characteristics of the agent itself (i.e. the biomass or protein extract of *T. chuii*) and the therapeutic effect to be achieved. It will also depend on the subject to be treated, the severity of the disease suffered by said subject, the chosen dosage form, etc. For this reason, the doses that may be mentioned in this invention must be considered only as guides for the person skilled in the art, who must adjust the doses depending on the aforementioned variables. In an embodiment, the effective amount produces the amelioration of one or more symptoms of the disease that is being treated. Even though individual needs vary, determination of optimal ranges for therapeutically effective amounts of the compounds according to the invention belongs to the common experience of those experts in the art. In general, the dosage needed to provide an effective treatment, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the compound is administered as part of a combination of drugs.

In a particular embodiment, the pharmaceutical composition of the medical use of the invention comprises the biomass of *T. chuii* previously described. In another particular embodiment, the pharmaceutical composition of the medical use of the invention comprises the protein extract of *T. chuii* previously described.

In a preferred embodiment, the male patient of the first aspect of the invention is characterized in that said subject shows male infertility.

The term "infertility" as used herein refers to a disease of the reproductive system defined by the failure to achieve a clinical pregnancy after 12 months or more of regular unprotected sexual intercourse. The expression "male infertility" as used herein refers to infertility when diagnosed in a male subject. Male infertility can be due to very different causes. Common causes of male infertility are alterations in one or several semen parameters, such as the volume of the semen sample, approximate number of total sperm cells, sperm motility or forward progression, percentage of sperm with DNA fragmentation, number of dead sperm cells in the semen or concentration of leukocytes in the semen. Alterations or deficiencies in one or several semen parameters can lead to different disorders, which can be classified as oligozoospermia, aspermia, hypospermia, azoospermia, teratozoospermia, asthenozoospermia, necrozoospermia, leukospermia, high SDF or a high oxidative stress in semen (which can lead to an increase of DNA oxidation and thus in the percentage of sperm with 8-hydroxy,2'-deoxyguanosine, and which is associated with high static Oxidation-Reduction Potential levels). Additionally, disorders characterized by the combination of two or more of said disorders can also occur, such as in the case of oligoasthenozoospermia, oligoasthenoteratozoospermia, oligoteratozoospermia, or asthenoteratozoospermia. The alteration of the semen parameters observed in said disorders can be due to a known cause; however, in a high percentage of cases, the cause of said alterations is unknown and are thus considered idiopathic disorders.

The expression "idiopathic" as used herein to refer to a disease or disorder is understood as any disease or disorder with unknown cause, or with apparent spontaneous origin. Therefore, the term "idiopathic" when applied to any of the diseases or disorders described herein, such as male infertility, oligozoospermia, asthenozoospermia, teratozoospermia, or high SDF, refers to the corresponding disease or disorder when the cause that originated it is unknown.

In a particular embodiment, the infertility is an idiopathic infertility.

The term "semen" or "seminal fluid", as used herein refers to the fluid that, in a healthy subject, comprises the sperm cells, produced by and released from the male reproductive organ. In humans, semen comprises various enzymes and fructose apart from the sperm cells. These elements promote the survival of the sperm cells as well as provide medium for them to swim. The process that results in the release of semen is termed "ejaculation", and the semen released is known as an "ejaculate". As the sperm cells pass through the ejaculatory ducts they become mixed with fluids mainly from seminal vesicles, prostate, and bulbourethral glands. The typical components of semen are as follows: spermatozoa (2-5%) produced and released from the testes, seminal vesicle secretions (65-75%, i.e. comprised of amino acids, citrate, flavins, fructose, and certain enzymes), prostate secretions (25-30%, i.e. comprised of acid phosphatase, citric acid, fibrinolysin, proteolytic enzymes, zinc, etc.), and bulbourethral gland secretions (<1%, i.e. contains galactose and mucus).

The term "sperm" refers to the plurality of sperm cells or spermatozoa comprised in semen.

The term "sperm cell" or "spermatozoon" as used herein refers to the mature male germ cell which can fertilize a mature ovum (secondary oocyte) in sexual reproduction. The spermatozoon develops in the seminiferous tubules of the testes. It is formed by a head, and a tail, wherein the tail is composed of a midpiece, a principal piece and an end piece. The head comprises the nucleus with densely coiled chromatin fibers surrounded by a flattened sac called the acrosome, containing enzymes involved in the penetration of the oocyte. The tail or flagellum provides the motion to the spermatozoa. The neck or midpiece, contains mitochondria that upon ATP production, provides energy for the motion of the spermatozoon. The characteristics of morphologically normal head, midpiece and principal piece of a spermatozoon are provided in the definition of "morphologically normal spermatozoa" below. The developmental stages of the spermatozoon are the spermatogonium, spermatocyte, spermatid, and finally spermatozoon.

The expression "semen sample" as used herein, refers to a sample comprising or consisting of semen from a male patient. In a preferred embodiment, said sample comprises the semen of 1, 2, 3, 4, 5, 6, 7, 8, 9, or 10 ejaculates from a male patient, preferably of 2 ejaculates from the male patient, more preferably of 1 ejaculate from the male patient. In a more preferred embodiment, the semen sample consists on the semen of any of the number of ejaculates just indicated, preferably on the semen of 1 ejaculate from a male patient. Thus, in a preferred embodiment, the volume of semen in a sample of semen of a patient or subject is equal to the volume of an ejaculate of said patient or subject. In another preferred embodiment, the volume of a sample of semen of a patient or subject is the volume of an ejaculate of said patient or subject. In addition, a semen parameter in a sample of semen of a patient or subject corresponds to said semen parameter in an ejaculate of semen of said patient or subject. Said ejaculate is that comprised in said semen sample. Said semen parameters include total number of spermatozoa, concentration of spermatozoa, volume of semen, percentage of morphologically normal spermatozoa, percentage of progressively motile spermatozoa, percentage of live spermatozoa, percentage of immotile spermatozoa. In a certain embodiment, a semen sample of a patient or subject refers to the semen of an ejaculate of said patient or subject, and vice versa. The reference value for the semen parameters are herein provided with respect to the semen of an ejaculate. Therefore, in a particular embodiment, the reference value of a semen parameter corresponds to the reference value for the semen parameter in a semen sample. Methods to obtain and to preserve a semen sample are well-known by an expert in the field and include the methods for the collection of semen samples described in "WHO laboratory manual for the Examination and processing of human semen", 2010, fifth edition.

In a preferred embodiment, any of the semen samples referred in any of the embodiments of any of the aspects of the invention are obtained after at least 1 day, at least 2, at least 3, at least 4, at least 5, at least 6, at least 7 at least 8, at least 9, at least 10, at least 15, at least 20, at least 25, at least 30 days of sexual abstinence. In a more preferred embodiment, any of said samples is obtained after at least 2 days of sexual abstinence.

In another preferred embodiment, any of the semen samples referred in any of the embodiments of any of the aspects of the invention are obtained after less than 5, less than 6, less than 7, less than 8, less than 9, less than 10, less than 11, less than 15, less than 20, less than 25, less than 30 days of sexual abstinence. In a more preferred embodiment, any of said samples are obtained after less than 7 days of sexual abstinence.

In a particular embodiment, any of the semen samples referred in any of the embodiments of any of the aspects of the invention are obtained after at least 2 days but after less than 5, less than 6, less than 7, less than 8, less than 9, less than 10, less than 11, less than 15, less than 20, less than 25, less than 30 days of sexual abstinence, preferably after less than 7 days of sexual abstinence.

In another particular embodiment, any of the semen samples referred in any of the embodiments of any of the aspects of the invention are obtained after at least 3 days but after less than 5, less than 6, less than 7, less than 8, less than 9, less than 10, less than 11, less than 15, less than 20, less than 25, less than 30 days of sexual abstinence, preferably after less than 7 days of sexual abstinence.

In another particular embodiment, any of the semen samples referred in any of the embodiments of any of the aspects of the invention are obtained after at least 4 days but after less than 5, less than 6, less than 7, less than 8, less than 9, less than 10, less than 11, less than 15, less than 20, less than 25, less than 30 days of sexual abstinence, preferably after less than 7 days of sexual abstinence.

In another particular embodiment, any of the semen samples referred in any of the embodiments of any of the aspects of the invention are obtained after at least 5 days but after less than 6, less than 7, less than 8, less than 9, less than 10, less than 11, less than 15, less than 20, less than 25, less than 30 days of sexual abstinence, preferably after less than 7 days of sexual abstinence.

In another particular embodiment, any of the semen samples referred in any of the embodiments of any of the aspects of the invention are obtained after at least 6 days but after less than 7, less than 8, less than 9, less than 10, less than 11, less than 15, less than 20, less than 25, less than 30 days of sexual abstinence, preferably after less than 7 days of sexual abstinence.

In another particular embodiment, any of the semen samples referred in any of the embodiments of any of the aspects of the invention are obtained after at least 7 days but after less than 8, less than 9, less than 10, less than 11, less than 15, less than 20, less than 25, less than 30 days of sexual abstinence, preferably after less than 7 days of sexual abstinence.

In a preferred embodiment, any of the semen samples referred in any of the embodiments of any of the aspects of the invention are obtained after at least 2 days but after less than 7 days of sexual abstinence.

The expression "sexual abstinence" as used herein refers to the absence of ejaculation by the male subject for a certain period of time. In a preferred embodiment, the semen samples of any of the aspects of the invention are obtained from one or more ejaculates from the male subject, preferably from one ejaculate from the male subject.

Therefore, in another preferred embodiment, sexual abstinence as used herein also refers to the absence of obtaining (i.e. collection) a sample of semen from said male patient.

The term "treatment", as used in the first aspect of the invention, refers to any type of therapy, which is aimed at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or, at least, symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of the alteration of a parameter associated to said disorder.

In a particular embodiment, the treatment referred in the first aspect of the invention comprises the administration of the biomass of *T. chuii*, the protein extract of *T. chuii*, or the pharmaceutical composition as defined herein. The biomass of *T. chuii*, the protein extract of *T. chuii*, or pharmaceutical composition for use according to the invention, can be administered to a subject by any suitable route of administration, for example, parenteral (e.g., intramuscular, intravenous, subcutaneous, nasal, etc.), enteral (i.e., oral, rectal, etc.), topical, etc. In a preferred embodiment, the biomass of *T. chuii*, the protein extract of *T. chuii*, or the pharmaceutical composition referred in the first aspect of the invention is administered orally.

The terms "subject", "patient" or "individual" are used herein interchangeably to refer to any member of the animal kingdom and can be a vertebrate, such as, a fish, a bird, a reptile, an amphibian or a mammal, including a human, non-human primate, horse, pig, rabbit, dog, sheep, goat, cow, bird, cat, guinea pig or rodent. Preferably, the subject is a mammal, more preferably a human.

In a particular embodiment, the subject has oligozoospermia. In a more particular embodiment, the subject has idiopathic oligozoospermia.

The term "oligozoospermia" as used herein refers to a disorder of a male subject or male patient, characterized in that the semen of the male patient shows a total number of spermatozoa per ejaculate, or concentration of spermatozoa, below the LRL stablished by the WHO ("WHO laboratory manual for the Examination and processing of human semen", 2010, fifth edition).

The term "total number of spermatozoa" or "total sperm number" as used herein, refers to the total number of spermatozoa per ejaculate.

The term "concentration of spermatozoa" or "sperm concentration", as used herein, refers to the total number of spermatozoa per ejaculate divided by the volume of the ejaculate.

In a preferred embodiment, when a male subject has oligozoospermia, at least 1, at least 2, at least 3, at least 4, at least 5, at least 6, at least 7, at least 8, at least 9, at least 10, preferably at least 2 samples of semen of a male subject must show a total number of spermatozoa per ejaculate, and/or a concentration of spermatozoa, below a reference value.

The term "reference value", as used herein, relates to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested. In a particular embodiment, the reference value is obtained from one or more male subjects, preferably healthy subjects, more preferably male subjects considered fertile.

In a particular embodiment, the reference value for oligozoospermia is the LRL established by the WHO ("WHO laboratory manual for the Examination and processing of human semen", 2010, fifth edition). The WHO establishes in said manual the LRL for total sperm number as $39*10^6$ per ejaculate, and the LRL for sperm concentration as $15*10^6$ per ml of semen. Methods to determine the total number of spermatozoa per ejaculate, or the concentration of spermatozoa in the semen of a male subject, or in a semen sample of a male subject, are well known by a person skilled in the art. Non-limiting examples of said methods include the methods for counting spermatozoa in semen samples, or for determining the number of spermatozoa in a semen sample, described in "WHO laboratory manual for the Examination and processing of human semen", 2010, fifth edition, in particular, the methods described in sections 2.7-2.8 of said document.

In a particular embodiment, the subject has aspermia. In a more particular embodiment, the subject has idiopathic aspermia.

The term "aspermia" as used herein refers to the disorder characterized in that a male subject does not release semen. This disorder can be due to an absence of or to a retrograde ejaculation. Methods to determine if a male subject shows aspermia are well-known by an expert in the field and include methods being part of common general knowledge, to determine the incapacity of a subject to ejaculate semen under any condition. Methods to determine retrograde ejaculation are described in "WHO laboratory manual for the Examination and processing of human semen", 2010, fifth edition.

In a particular embodiment, the subject has hypospermia. In a more particular embodiment, the subject has idiopathic hypospermia.

The term "hypospermia" as used herein refers to the disorder characterized in that the volume of semen per ejaculate in a male subject is unusually low, i.e. below a LRL.

The term "volume of semen" as used herein, refers to the volume of semen per ejaculate.

In a preferred embodiment, when a male subject has hypospermia, at least 1, at least 2, at least 3, at least 4, at least 5, at least 6, at least 7, at least 8, at least 9, at least 10, preferably at least 2 ejaculates of the male subject must show a volume of semen below a reference value. In a particular embodiment, said reference value is the LRL established by WHO in "WHO laboratory manual for the Examination and processing of human semen", 2010, fifth edition. In a particular embodiment, when a male subject has hypospermia and a semen sample of said male subject comprises the semen of only one ejaculate, at least 1, at least 2, at least 3, at least 4, at least 5, at least 6, at least 7, at least 8, at least 9, at least 10, preferably at least 2 semen samples from said male subject must show a volume of semen per ejaculate below a reference value, wherein the reference value is preferably the LRL established by the WHO in "WHO laboratory manual for the Examination and processing of human semen", 2010, fifth edition. The LRL for the volume of semen of an ejaculate established by the WHO in said manual is 1.5 ml. Methods to determine the volume of semen of an ejaculate, or the volume of semen per ejaculate of a semen sample, are well known by a person skilled in the art. Non-limiting examples of said methods include the methods for sample collection and for measuring the volume of semen samples described in "WHO laboratory manual for the Examination and processing of human semen", 2010, fifth edition, in particular in section 2.2 and 2.3.4 in said document.

In a particular embodiment, the subject has azoospermia. In a more particular embodiment, the subject has idiopathic azoospermia.

The term "azoospermia" as used herein refers to the disorder characterized in that the semen of a male subject shows absence of spermatozoa, in testicular semen and/or in the semen of the ejaculate, given as a number of spermatozoa below the limit of quantification for the assessment method employed. In a preferred embodiment, when a male patient has azoospermia, at least 1, at least 2, at least 3, at least 4, at least 5, at least 6, at least 7, at least 8, at least 9, at least 10, preferably at least 2 samples of semen of said male subject must show absence of spermatozoa, given as a number of spermatozoa below the limit of quantification for the assessment method employed. Methods to determine the absence of spermatozoa in the semen of a male patient or in a sample of semen of a male patient are well known by a person skilled in the art. Non-limiting examples of said methods include the methods for determining the number of spermatozoa in a semen sample and the methods to determine the number of spermatozoa in a semen sample with low sperm number described in "WHO laboratory manual for the Examination and processing of human semen", 2010, fifth edition, in particular, in particular the methods described in sections 2.7-2.11.

In a particular embodiment, the subject has teratozoospermia. In a more particular embodiment, the subject has idiopathic teratozoospermia.

The term "teratozoospermia" as used herein refers to a disorder characterized in that the semen of a male subject shows a percentage of morphologically normal spermatozoa below a LRL.

The term "percentage of morphologically normal spermatozoa" as used herein, refers to the percentage of morphologically normal spermatozoa with respect to the total number of spermatozoa per ejaculate.

In a preferred embodiment, when a male patient has teratozoospermia, at least 1, at least 2, at least 3, at least 4, at least 5, at least 6, at least 7, at least 8, at least 9, at least 10, preferably at least 2 samples of semen of said male subject show a percentage of morphologically normal spermatozoa below a reference value. In a particular embodiment, the reference value is the LRL established by the WHO in "WHO laboratory manual for the Examination and processing of human semen", 2010, fifth edition. The WHO establishes said manual the LRL for the percentage of morphologically normal spermatozoa as 4%. Methods to determine the percentage of morphologically normal spermatozoa in the semen of a male subject, or in a semen sample of a male subject, are well known by a person skilled in the art. Non-limiting examples of said methods include the methods described in "WHO laboratory manual for the Examination and processing of human semen", 2010, fifth edition for determining the percentage of morphologically normal spermatozoa in semen samples, in particular, the methods described in sections 2.13-2.17 of said document.

The expression "morphologically normal spermatozoa" as used herein, refers to spermatozoa wherein:

i) the head is smooth, regularly contoured and generally oval in shape. It comprises a well-defined acrosomal region comprising 40-70% of the head area. The acrosomal region contains no large vacuoles, and not more than two small vacuoles, which do not occupy more than 20% of the sperm head. The post-acrosomal region does not contain any vacuoles;

ii) the midpiece is slender, regular and about the same length as the sperm head. The major axis of the midpiece is aligned with the major axis of the sperm head. Residual cytoplasm is considered an anomaly only when in excess, i.e. when it exceeds one third of the sperm head size;

iii) the principal piece, has a uniform calibre along its length, it is thinner than the midpiece, and is approximately 45 µm long (about 10 times the head length). It may be looped back on itself, provided there is no sharp angle indicative of a flagellar break.

In a particular embodiment, the subject has asthenozoospermia. In a more particular embodiment, the subject has idiopathic asthenozoospermia.

The term "asthenozoospermia" as used herein refers to a disorder characterized in that the semen of a male subject shows a percentage of progressively motile (PR) spermatozoa below a LRL.

The term "percentage of progressively motile spermatozoa" as used herein, refers to the percentage of progressively motile spermatozoa with respect to the total number of spermatozoa per ejaculate.

In a preferred embodiment, when a male patient has asthenozoospermia, at least 1, at least 2, at least 3, at least 4, at least 5, at least 6, at least 7, at least 8, at least 9, at least 10, preferably at least 2 samples of semen of said male subject show a percentage of progressively motile (PR) spermatozoa below a reference value. In a particular embodiment, the reference value is the LRL established by the WHO in "WHO laboratory manual for the Examination and processing of human semen", 2010, fifth edition. The WHO establishes in said manual the LRL for the PR as 32%. Methods to determine the percentage of PR spermatozoa in the semen of a male subject, or in a semen sample of a male subject, are well-known by an expert in the field. Non-limiting examples of said methods include the methods described in "WHO laboratory manual for the Examination and processing of human semen", 2010, fifth edition for determining the percentage of spermatozoa with PR in semen samples, in particular, the methods described in section 2.5 of said document. The expression "progressively motile spermatozoa" as used herein, refers to spermatozoa that move actively, either linearly or in a large circle, regardless of speed.

In a particular embodiment, the subject has necrozoospermia. In a more particular embodiment, the subject has from idiopathic necrozoospermia. The term "necrozoospermia" as used herein refers to a disorder characterized in that the semen of a male subject shows a low percentage of live spermatozoa in the ejaculate.

The term "percentage of live spermatozoa" as used herein, refers to the percentage of live spermatozoa with respect to the total number of spermatozoa in an ejaculate.

In a preferred embodiment, when a male patient has necrozoospermia, at least 1, at least 2, at least 3, at least 4, at least 5, at least 6, at least 7, at least 8, at least 9, at least 10, preferably at least 2 samples of semen of a male subject show a percentage of live spermatozoa below a reference value. In a particular embodiment, the reference value is preferably the LRL established by the WHO in "WHO laboratory manual for the Examination and processing of human semen", 2010, fifth edition. The WHO establishes in said manual the LRL for live spermatozoa in a semen sample as 58%. Methods to determine percentage of live spermatozoa in the semen of a male subject, or in a sample of semen of a male subject, are well known by a person skilled in the art. Non-limiting examples of said methods include those to assess the amount of spermatozoa with an intact membrane in a sample described in "WHO laboratory manual for the Examination and processing of human semen", 2010, fifth edition, in particular the vitality tests disclosed in section 2.6 of said document.

In a particular embodiment, the subject has leukospermia. In a more particular embodiment, the subject has from idiopathic leukospermia.

The term "leukospermia", "leucospermia", "leukocytospermia", or "pyospermia", as used herein refers to a condition characterized in that the semen of a male subject shows a concentration of leukocytes above a LRL. The term "concentration of leukocytes", as used herein, refers to the total concentration of leukocytes per ejaculate divided by the volume of the ejaculate.

In a preferred embodiment, when a male patient has leukospermia, at least 1, at least 2, at least 3, at least 4, at least 5, at least 6, at least 7, at least 8, at least 9, at least 10, preferably at least 2 samples of semen of said male subject show a concentration of leukocytes above a reference value. In a particular embodiment, the reference value is the LRL established by the WHO in "WHO laboratory manual for the Examination and processing of human semen", 2010, fifth edition. The WHO establishes in said manual the LRL for the concentration of leukocytes as $1*10^6$ leukocytes per ml when detected by a peroxidase test, i.e. of peroxidase-positive leukocytes per ml. Said test is well-known by a skilled person and is described in "WHO laboratory manual for the Examination and processing of human semen", 2010, fifth edition. Methods to determine the concentration of leukocytes in the semen of a male subject, or in a semen sample of a male subject, are well known by an expert in the field. Non-limiting examples of said methods includes the method to determine the presence of leukocyte in semen samples based on the peroxidase test and described in "WHO laboratory manual for the Examination and processing of human semen", 2010, fifth edition, in particular, the methods described in section 2.18 of said document.

In a particular embodiment, the patient has a disorder characterized by a percentage of SDF above a reference value. In a more particular embodiment, said disorder is an idiopathic disorder.

The expression "sperm DNA fragmentation" or "SDF" as used herein refers to DNA damage, i.e. single and/or double DNA breaks, in sperm cells (from semen released upon ejaculation or from testicular semen). Thus, the percentage of SDF, or the DNA fragmentation index (DFI) as used herein refers to the percentage of sperm cells showing DNA damage, i.e. single and/or double DNA breaks, with respect to the total number of spermatozoa in an ejaculate. A male subject with a certain percentage of SDF is understood as a subject characterized in that a sample of semen, or an ejaculate, from said subject shows said percentage of SDF. DNA repair does occur in developing sperm but it is terminated as transcription and translation stops post-spermiogenesis. As a result, sperm have no mechanism to repair DNA damage that occurs during their transit and storage in the epididymis or post-ejaculation, which explains the susceptibility of sperm to DNA fragmentation and the presence of DNA fragmentation in the sperm of every male subject. As understood by a skilled person, when the semen of a male subject has a high percentage of SDF, the capacity of the semen of said subject to reach fertilization is low. In general terms, a semen showing a percentage of DNA fragmentation equal or below a percentage around 15% is considered of good quality, i.e. with a high capacity to accomplish fertilization. However, if the percentage of DNA fragmentation is equal to or higher than a percentage, such as around 16% in some cases, the quality of the semen is considered to be poor, i.e. with a low capacity to accomplish fertilization. Therefore, a high percentage of SDF in a male subject is considered a disorder. If the cause of said disorder is unknown, it is considered an idiopathic disorder. The expression "a sample of semen shows x % of SDF", or "a sample of semen shows a DNA fragmentation index (DFI) of x %", as used herein, refers to a sample of semen wherein x % of the sperm cells within the semen of said sample show DNA fragmentation. Thus, as a person skilled in the field will understand, a sample of semen that shows a percentage of SDF equal or below 15% is a sample of semen wherein 15% or less of sperm cells show SDF and is generally considered a sample of semen of good quality, i.e. with a high capacity to accomplish fertilization. A sample of semen that shows a percentage of SDF equal or higher than 16% is a sample of semen wherein 16% or more of sperm cells show SDF and is thus, in some cases, considered a sample of semen of poor quality, i.e. with a low capacity to accomplish fertility. In a preferred embodiment, when a male patient has a disorder characterized by a percentage of SDF above a reference value, at least 1, at least 2, at least 3, at least 4, at least 5, at least 6, at least 7, at least 8, at least 9, at least 10, preferably at least 2 semen samples of said male subject show a percentage of SDF above reference value, wherein said reference value is preferably 16%. Analogously, when a male patient does not have a disorder characterized by a percentage of SDF above a reference value, at least 1, at least 2, at least 3, at least 4, at least 5, at least 6, at least 7, at least 8, at least 9, at least 10, preferably at least 2 semen samples of said male subject show a percentage of SDF below said reference value, wherein said reference value is preferably 16%.

Methods to determine the percentage of SDF, or a DFI, in the semen of a male subject, or in a semen sample from a male subject, are well-known by an expert in the field. Non-limiting examples of said methods include Toluidine blue staining, CMA3 staining, Acridine orange (AO) assay, SCSA, SCD test/Halo, Comet assay, TUNEL assay as described in Manesh Kumar Panner Selvam and Ashok Agarwal, 2018, Arab J Urol. 16(1): 65-76.

In a particular embodiment, the patient has a disorder characterized by level of 8-OHdG, a ratio $8\text{-OHdG}/10^5$ dG, or a percentage of 8-OH-dG positive sperm cells, in semen above a reference value. In a more particular embodiment, said disorder is an idiopathic disorder. The term "8-hydroxy, 2-deoxyguanosine", or "8-OHdG", as used herein, refers to an oxidized guanine base adduct formed when an OH-radical damages DNA. It is considered a marker of DNA oxidation. Reactive Oxygen Species (ROS) can damage DNA directly thus generating oxidized DNA adducts (such as 8-OHdG), which then lead to abasic sites that destabilize the DNA structure and cause subsequent single-strand breaks. Thus, the presence of 8-OHdG can be related with the DNA oxidation and with the subsequent appearance of DNA strand breaks. Indeed, DNA repair is limited in spermatozoa and only occurs during specific stages of spermatogenesis. In particular, repair mechanisms are no longer active during nuclear condensation in the epididymis, although spermatozoa are exposed to oxidative damage in the epididymis and during transport in the seminal fluid. The DNA adducts induced by oxidative stress may be repaired by the oocyte, but single- or double-stranded DNA breaks may not. Thus, the presence of 8-OHdG in sperm cells can lead to the appearance of DNA fragmentation, and has a significant impact on fertilization and pregnancy outcome. Thus, the amount of 8-OH-dG in sperm cells in semen can be measured to determine the level of DNA damage in the sperm cells in semen resulting from oxidative stress. Thus, in a particular embodiment, in all the aspects of the present invention, the disorder characterized by a level of 8-OH-dG, a ratio 8-OH-dG/$10^5$ dG, or a percentage of 8-OH-dG positive sperm cells, in semen above a reference value refers to a disorder characterized by a high level of DNA oxidation in semen. In another particular embodiment, in all the aspects of the present invention, the disorder characterized by a level of 8-OH-dG, a ratio 8-OH-dG/$10^5$ dG, or a percentage of 8-OH-dG positive sperm cells, in semen above a reference value refers to a disorder characterized by a high level of DNA damage in semen, preferably caused by oxidative stress in semen. In another embodiment, in all the aspects of the present invention, the disorder characterized by a level of 8-OH-dG, a ratio 8-OH-dG/$10^5$ dG, or a percentage of 8-OH-dG positive sperm cells, in semen above a reference value refers to a disorder characterized by a high oxidative stress in semen.

In a preferred embodiment, when a male patient has a condition characterized by a level of 8-OHdG in semen above a reference value, at least 1, at least 2, at least 3, at least 4, at least 5, at least 6, at least 7, at least 8, at least 9, at least 10, preferably at least 2 semen samples of said male subject show a level of 8-OHdG above a reference value. Analogously, when a male patient does not have a condition characterized by a level of 8-OHdG in semen above a reference value, at least 1, at least 2, at least 3, at least 4, at least 5, at least 6, at least 7, at least 8, at least 9, at least 10, preferably at least 2 semen samples of said male subject show a level of 8-OH-dG below a reference value.

In another preferred embodiment, when a male patient has a condition characterized by a ratio 8-OH-dG/$10^5$ dG in semen above a reference value, at least 1, at least 2, at least 3, at least 4, at least 5, at least 6, at least 7, at least 8, at least 9, at least 10, preferably at least 2 semen samples of said male subject show a ratio 8-OH-dG/$10^5$ dG above a reference value. Analogously, when a male patient does not have a condition characterized by a ratio 8-OH-dG/$10^5$ dG in semen above a reference value, at least 1, at least 2, at least 3, at least 4, at least 5, at least 6, at least 7, at least 8, at least 9, at least 10, preferably at least 2 semen samples of said male subject show a ratio 8-OH-dG/$10^5$ dG below a reference value.

In another preferred embodiment, when a male patient has a condition characterized by a percentage of 8-OH-dG positive sperm cells in semen above a reference value, at least 1, at least 2, at least 3, at least 4, at least 5, at least 6, at least 7, at least 8, at least 9, at least 10, preferably at least 2 semen samples of said male subject show a percentage of 8-OH-dG positive sperm cells above a reference value. Analogously, when a male patient does not have a condition characterized by a percentage of 8-OH-dG positive sperm cells in semen above a reference value, at least 1, at least 2, at least 3, at least 4, at least 5, at least 6, at least 7, at least 8, at least 9, at least 10, preferably at least 2 semen samples of said male subject show a percentage of 8-OH-dG positive sperm cells below a reference value.

The expression "the level of 8-OH-dG in semen", as used herein, refers to the amount of 8-OH-dG as defined above, detected in semen. In a particular embodiment, the level of 8-OH-dG in semen refers to the level of 8-OH-dG as defined above in an ejaculate, or in a semen sample. The level of 8-OH-dG in semen or in a semen sample can be measured by different methods. It is commonly measured using an immunofluorescence method or a commercial kit, such as the OxyDNA kit followed by light microscopy, fluorescence microscopy or flow cytometry, preferably an immunofluorescence method followed by flow cytometry. Any of said methods is well known by an expert in the field, and can be carried as described in Vorilhon et al., 2018, Human reproduction, 33(4): 553-562. In this case, the level of 8-OH-dG can be expressed as the Mean Intensity Fluorescence (MIF) of a sample and measured in arbitrary units (a.u.). The reference value for the level of 8-OH-dG in a semen sample is 300, 325, 350, 375, 400, 425, 450, 475, 500, 510, 515, 520, 525, 530, 535, 540, 545, 550, 551, 552, 553, 554, 555, 556, 557, 558, 559, 560, 562, 565, 567, 570, 575, 580, 585, 590, 595, 600, 625, 650, 675, 700, 750, 800, 850, 900 arbitrary units, preferably at least 552 arbitrary units, when the method is based in immunofluorescence followed by flow cytometry, as that described in Vorilhon et al., 2018, Human reproduction, 33(4): 553-562. As indicated above, the level of 8-OH-dG in semen can refer to the level of 8-OH-dG in an ejaculate or in a semen sample, and thus, in a particular embodiment, the reference value for the parameter level of 8-OH-dG in semen is any of those provided in the present specification for the parameter level of 8-OH-dG in a semen sample.

The expression "a ratio 8-OH-dG/$10^5$ dG in semen" as used herein, refers to the amount of 8-OH-dG as defined above, detected in semen, and divided by the amount of dG detected in semen expressed by groups of $10^5$, wherein dG refers to dioxyguanosine. In a particular embodiment, the ratio 8-OH-dG/$10^5$ dG in semen refers to the ratio 8-OH-dG/$10^5$ dG as just defined, in an ejaculate, or in a semen sample. The ratio 8-OH-dG/$10^5$ dG can be measured by different methods. Non-limiting examples of said methods include high-performance liquid chromatography equipped with electrochemical detection (HPLC-EC), or gas chromatography-mass spectrometry (GC/MS). Said methods are well known by an expert in the field, and can be carried out, for instance, following the indications found in Shen and Ong., 2000, Free Radical Biology and Medicine, 28(4): 529-536. In this case, the reference value of a ratio 8-OH-dG/$10^5$ dG in a sample of semen is 1.0, 1.1, 1.2, 1.3, 1.4, 1.5, 1.6, 1.7, 1.8, 1.9, 2.0, 2.25, 2.5, 2.75, 3.0, 3.5, 4.0, 4.5, 5.0, 5.5, 6.0, 6.5, 7.0, 7.5, 8.0, 8.5, 9.0, 9.5, 10.0, 10.5, 11.0, 12, 13, 14, 15, 16, 17, 18, 19, 20, 30, 40, 50, 60, 80, 90, 100, preferably 1.5 8-OH-dG/$10^5$ dG. As indicated above, the ratio of 8-OH-dG/$10^5$ dG in semen can refer to the ratio of 8-OH-dG/$10^5$ dG in an ejaculate or in a semen sample, and thus, in a particular embodiment, the reference value for the parameter 8-OH-dG/$10^5$ dG in semen is any of those provided in the present specification for the parameter 8-OH-dG/$10^5$ dG in a semen sample.

The expression "a percentage of 8-OH-dG positive sperm cells in semen", or "the percentage of 8-OH-dG positive sperm cells", or "the percentage of sperm cells with 8-OH-dG", as used herein, refers to the percentage of sperm cells detected positive for 8-OH-dG with respect to the total number of spermatozoa in semen. In a particular embodiment, the percentage of 8-OH-dG positive sperm cells in semen refers to the percentage of 8-OH-dG as just defined, in an ejaculate, or in a semen sample. The percentage of 8-OH-dG positive sperm cells in semen can be measured by different methods. Non-limiting examples of said methods include immunofluorescence-based methods or a commercial kit, such as the OxyDNA kit followed by light microscopy, fluorescence microscopy or flow cytometry, preferably an immunofluorescence-based method followed by flow cytometry. Any of said method is well known by an expert in the field, and can be carried as described in Vorilhon et al., 2018, Human reproduction, 33(4): 553-562. In this case, the reference value for the percentage of 8-OH-dG positive sperm cells in a semen sample is 20%, 25%, 30%, 35%, 40%, 45%, 50%, 52%, 55%, 57%, 60%, 61%, 62%, 63%, 64%, 64.5%, 65%, 65.2%, 65.5%, 65.6%, 65.7%, 65.8%, 65.9%, 66%, 66.1%, 66.2%, 66.3%, 66.4%, 66.5%, 66.7%, 67%, 67.5%, 68%, 68.5%, 69%, 69.5%, 70%, 71%, 72%, 73%, 74%, 75% 77%, 80%, 82%, 875%, 87%, 90%, 95%, 97%, 98%, 99% of 8-OH-dG positive sperm cells with respect to the total number of spermatozoa in a semen sample, preferably of 65.8% of 8-OH-dG positive sperm cells with respect to the total number of spermatozoa in a semen sample. As indicated above, the percentage of 8-OH-dG positive sperm cells in semen can refer to the percentage of 8-OH-dG positive sperm cells in an ejaculate or in a semen sample, and thus, in a particular embodiment, the reference value for the parameter percentage of 8-OH-dG positive sperm cells in a semen is any of those provided in the present specification for the parameter percentage of 8-OH-dG positive sperm cells in a semen sample.

In a particular embodiment, the patient has a disorder characterized by a static Oxidation-reduction Potential (sORP) above a reference value. In a more particular embodiment, said disorder is an idiopathic disorder.

The expression "static Oxidation-Reduction Potential", or "sORP", as used herein, refers to the measure of the balance between total oxidants and reductants in a biological system which can be considered as a measure of the oxidative stress in said sample. The expression "static Oxidation-Reduction Potential in semen", or "sORP in semen", as used herein, refers to the value of the static Oxidation-Reduction Potential as defined above when the biological system is semen. Thus, sORP in semen can be considered a measure of the level of oxidative stress in semen. Thus, in a particular embodiment, the disorder characterized by a sORP in semen above a reference value referred in any aspect of the present invention is a disorder characterized by a high oxidative stress in semen.

In particular embodiment, the expression "sORP in semen" refers to the sORP in an ejaculate, or in a semen sample.

In a preferred embodiment, when a male patient has a disorder characterized by a sORP in semen above a reference value, at least 1, at least 2, at least 3, at least 4, at least 5, at least 6, at least 7, at least 8, at least 9, at least 10, preferably at least 2 samples of semen of said male subject show a sORP above a reference value.

The sORP in semen, or in a semen sample is directly related with transfer electrons from reductants to oxidants present in samples of said semen, or the electric potential of said samples. Methods allowing measuring said transfer of electrons or the electric potential in semen or in a semen sample are well-known by an expert in the field. Non-limiting examples of methods allowing to measure the sORP in semen or in a semen sample include the MioXSYS System, as described in Agarwal A, Bui A D. Investig. Clin Urol. 2017; 58(6):385-399. The value in mV provided by said type of methods, is generally divided by the sperm concertation of the semen sample/s analyzed, so that the sORP is generally provided as mv/$10^6$ sperm/ml of semen. In a particular embodiment, the reference value for sORP in a semen sample is 0.5, 0.6, 0.7, 0.8, 0.9, 1.0, 1, 1.1, 1.2, 1.25, 0.27, 1.3, 10.31, 1.32, 1.33, 1.34, 1.35, 1.36, 1.37, 1.38, 1.39, 1.4, 1.41, 1.42, 1.43, 1.44, 1.45, 1.46, 1.47, 1.481, 1.49, 1.5, 1.51, 1.52, 1.53, 1.54, 1.55, 1.57, 1.6, 1.62, 1.65, 1.67, 1.7, 1.75, 1.8, 1.85, 1.9, 1.95, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.35, 5.6, 5.7, 5.8, 5.9, 6.0, 6.25, 6.5, 6.75, 7.0, 7.25, 7.5, 7.75, 8.0, 8.25, 8.5, 8.75, 9.0, 9.5, 10.0, 10.5, 11.0, 11.5, 12.0, 12.5, 13.0, 13.5, 14.0, 14.5, 15.0 mV/$10^6$ sperm/ml of semen, preferably 1.34 mV/$10^6$ sperm/ml of semen, more preferably 1.36 mV/$10^6$ sperm/ml of semen, even more preferably 1.48 mV/$10^6$ sperm/ml of semen. As indicated above, the sORP in semen can refer to the sORP in an ejaculate or in a semen sample, and thus, in a particular embodiment, the reference value for the parameter sORP in a semen is any of those provided in the present specification for the parameter sORP in a semen sample.

In a particular embodiment of the first aspect of the invention, the total number and/or concentration of spermatozoa in a sample of semen of the male patient after the treatment referred in the medical use of the invention is equal or above a reference value. Preferably, a total number and/or concentration of spermatozoa equal or above a reference value is observed in at least 1, at least 2, at least 3, at least 4, at least 5, at least 6, at least 7, at least 8, at least 9, at least 10, at least 15, at least 20 samples, preferably at least 2 samples of semen of the male patient after the treatment referred in the medical use of the invention.

In a preferred embodiment, the male patient of the medical use of the invention is as defined in any of the embodiments of the first aspect of the invention, preferably the patient has oligozoospermia, and the total number and/or the concentration of spermatozoa in a sample of semen of said patient after the treatment referred in said medical use is equal or above a reference value. Preferably, the total number of spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention. In another preferred embodiment, the concentration of spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient is as defined in any of the embodiments of the first aspect of the invention before the treatment referred in said aspect of the invention, more preferably the patient has oligozoospermia before said treatment, and the total number and/or concentration of spermatozoa in a sample of semen of said patient after said treatment is equal or above a reference value. Preferably, the total number of spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention. In another preferred embodiment, the concentration of spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention Methods to determine the number of spermatozoa and the concentration of spermatozoa in a semen sample have been provided above in the definition of "oligozoospermia".

The expression "total number of spermatozoa in a semen sample above a reference value", as used herein, refers to a total number of spermatozoa in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to the reference value.

The expression "total number of spermatozoa in a semen sample equal to a reference value", as used herein, refers to a total number of spermatozoa in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to a total number of spermatozoa in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "number of spermatozoa in a semen sample below a reference value", as used herein, refers to a total number of spermatozoa in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a particular embodiment, the reference value for the total number of spermatozoa is $25*10^5$, $30*10^5$, $39*10^5$, $1*10^6$, $5*10^6$, $10*10^6$, $20*10^6$, $25*10^6$, $30*10^6$, $39*10^6$, $32*10^6$, $35*10^6$, $40*10^6$, $45*10^6$, $50*10^6$, $60*10^6$, $80*10^6$, $1*10^7$, or $1*10^8$ sperm cells per ejaculate, preferably, $39*10^6$ sperm cells per ejaculate. In another preferred embodiment, the reference value for the total number of spermatozoa in a sample of semen corresponds to the LRL established by the WHO in "WHO laboratory manual for the Examination and processing of human semen", 2010, fifth edition, for the number of sperm per ejaculate, which is $39*10^6$ sperm cells per ejaculate.

The expression "concentration of spermatozoa in a semen sample above a reference value", as used herein, refers to a concentration of spermatozoa in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to the reference value.

The expression "concentration of spermatozoa in a semen sample equal to a reference value", as used herein, refers to any concentration of spermatozoa in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to any concentration of spermatozoa in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "concentration of spermatozoa in a semen sample below a reference value", as used herein, refers to a concentration of spermatozoa in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a particular embodiment, the reference value for the concentration of spermatozoa in a sample of semen is $5*10^5$, $10*10^5$, $15*10^5$, $50*10^5$, $1*10^6$, $5*10^6$, $10*10^6$, $15*10^6$, $20*10^6$, $25*10^6$, $50*10^6$, $75*10^6$, $10*10^7$, $25*10^7$, $50*10^7$, $75*10^7$, or $10*10^8$ spermatozoa per ml of semen, preferably $15*10^6$ spermatozoa per ml of semen. In a preferred embodiment, the reference value for the concentration of spermatozoa in a semen sample corresponds to the LRL established by the WHO in "WHO laboratory manual for the Examination and processing of human semen", 2010, fifth edition, for the concentration of spermatozoa per ml of semen, which is $15*10^6$ spermatozoa per ml of semen.

In another preferred embodiment, the reference value for the total number or concentration of spermatozoa in a semen sample of a male subject, is the total number or the concentration of spermatozoa in a sample of semen of said male patient obtained before the treatment referred in the first aspect of the invention. In another preferred embodiment, it refers to the total number or concentration of spermatozoa in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to the total number or concentration of spermatozoa in more than one sample, said reference value corresponds to the mean of the values of the parameter "total number of spermatozoa" or "concentration of spermatozoa" obtained in each of said samples. In a certain embodiment, said samples are each one obtained at a different time, before the treatment referred in the first aspect of the invention has started.

In another particular embodiment, the reference value for the total number of spermatozoa in a semen sample is lower than $25*10^5$, lower than $10*10^5$, lower than $1*10^5$, lower than $1*10^4$, lower than $1*10^3$, lower than $1*10^4$, lower than $1*10^2$, lower than 10 spermatozoa per ejaculate, preferably it is around 0 spermatozoa per ejaculate, more preferably it is 0 spermatozoa per ejaculate. In another particular embodiment, the reference value for the total number of spermatozoa in a semen sample is the limit of quantification of spermatozoa in a semen sample for the assessment method employed.

In another particular embodiment, since said reference value is the minimal one for the parameter "total number of spermatozoa in a semen sample", the expression "total number of spermatozoa in a semen sample below a reference value" refers to a total number of spermatozoa in a semen sample equal to said reference value. The expression "total number of spermatozoa in a semen sample equal to a reference value" refers to a total number of spermatozoa in a semen sample that is, or coincides with, said reference value. In another particular embodiment, the expression "total number of spermatozoa in a semen sample above a reference value" refers to any value higher than said reference value, preferably it refers to an absolute value different from 0. In a preferred embodiment it refers to at least 1, at least 2 at least 3, at least 4, at least 5, at least 10, at least 20, at least 100, at least $1*10^3$, at least $1*10^4$, at least $1*10^5$, at least $1*10^6$, at least $20*10^6$, at least $30*10^6$, at least $39*10^6$, at least $40*10^6$, at least $50*10^6$, at least $1*10^7$ spermatozoa per ejaculate, preferably at least $39*10^6$ spermatozoa per ejaculate.

In another particular embodiment, the reference value for the concentration of spermatozoa in a semen sample is lower than $5*10^5$, lower than $4*10^5$, lower than $1*10^5$, lower than $1*10^4$, lower than $1*10^3$, lower than $1*10^2$, lower than 10 spermatozoa per ml of semen, preferably it is around 0 spermatozoa per ml of semen, more preferably it is 0 spermatozoa per ml of semen. In another particular embodiment, the reference value for the concentration of spermatozoa in a semen sample is the limit of quantification of spermatozoa in a semen sample for the assessment method employed. In this case, since said reference value is the minimal one for the parameter "concentration of spermatozoa in a semen sample", the expression "concentration of spermatozoa in a semen sample below a reference value" refers to a concentration of spermatozoa in a semen sample equal to said reference value. The expression "concentration of spermatozoa in a semen sample equal to a reference value" refers to a concentration of spermatozoa in a semen sample that is, or coincides with, said reference value. In another particular embodiment, the expression "concentration of spermatozoa in a semen sample above a reference value" refers to any value higher than said reference value, preferably it refers to an absolute value different from 0. In a preferred embodiment, it refers to at least 1, at least 2 at least 3, at least 4, at least 5, at least 10, at least 20, at least 100, at least $1*10^3$, at least $1*10^4$, at least $1*10^5$, at least $1*10^6$, at least $15*10^6$, $20*10^6$, $25*10^6$, $50*10^6$, $75*10^6$, $10*10^7$, $50*10^7$ spermatozoa per ml of semen, preferably at least $15*10^6$ spermatozoa per ml of semen.

In another particular embodiment, the patient of the first aspect of the invention has azoospermia. Methods to determine if a subject has azoospermia have been provided above in the definition of azoospermia. In another particular embodiment, all the embodiments where the term "oligozoospermia" is used also apply herein, by substituting the term "oligozoospermia" by "azoospermia". The expression "before the treatment referred in the first aspect of the invention", or "before the start of the treatment referred in the first aspect of the invention", as used herein, refers to any moment before the treatment of the first aspect of the invention. In a preferred embodiment, it refers to a moment at least 1 hour, at least 2 hours, at least 5 hours, at least 6 hours, at least 8 hours, at least 10 hours, at least 12 hours, at least 24 hours, at least 1.5 days, at least 2 days, at least 4 days, at least 5 days, at least 6 days, at least 1 week, at least 1.5 weeks, at least 2 weeks, at least 3 weeks, at least 1 month, at least 2 months, at least 3 months, at least 4 months, at least 5 months, at least 6 months, at least 1 year, at least 1.5 years at least 2 years, at least 5 years, at least 10 years, preferably at least 1 month, more preferably at least 1 week, even more preferably at least 1 day, yet more preferably at least 1 hour before the start of said treatment.

The expression "after the treatment referred in the first aspect of the invention", or "after the treatment referred in the medical use of the invention", as used herein, refers to any moment after the treatment of the first aspect of the invention. In a preferred embodiment, it refers to a moment just after the end of said treatment, preferably, at least 1 hour, at least 2 hours, at least 5 hours, at least 6 hours, at least 8 hours, at least 10 hours, at least 12 hours, at least 24 hours, at least 1.5 days, at least 2 days, at least 4 days, at least 5 days, at least 6 days, at least 1 week, at least 1.5 weeks, at least 2 weeks, at least 3 weeks, at least 1 month, at least 2 months, at least 3 months, at least 4 months, at least 5 months, at least 6 months, at least 1 year, at least 1.5 years at least 2 years, at least 5 years, at least 10 years, preferably at least 1 month, more preferably at least 1 week, even more preferably at least 1 day, yet more preferably at least 1 hour after the end of said treatment.

In a particular embodiment of the first aspect of the invention, the percentage of progressive motile spermatozoa in a sample of semen of the male patient after the treatment referred in the medical use of the invention is equal or above a reference value. Preferably, the percentage of progressive motile spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has asthenozoospermia and the percentage of progressive motile spermatozoa in a sample of semen of said male patient after the treatment referred in the medical use of the invention is equal or above a reference value. Preferably, the percentage of progressive motile spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a certain embodiment, the male patient is as defined in any of the embodiments of the first aspect of the invention before the treatment referred in said aspect of the invention, preferably the patient has asthenozoospermia before said treatment and the percentage of progressive motile spermatozoa in a sample of semen of said male patient after said treatment is equal or above a reference value. Preferably, the percentage of progressive motile spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

The expression "progressively motile" has been defined above. Methods to determine the percentage of progressively motile spermatozoa in a semen sample have been provided above in the definition of asthenozoospermia.

The expression "percentage of progressive motile spermatozoa in a semen sample above a reference value" as used herein, refers to any percentage of progressive motile spermatozoa in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "percentage of progressive motile spermatozoa in a semen sample equal to a reference value", as used herein, refers to any percentage of progressive motile spermatozoa in semen sample which is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to any percentage of progressive motile spermatozoa in semen sample which is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "percentage of progressive motile spermatozoa in a semen sample below a reference value", as used herein, refers to a percentage of progressive motile spermatozoa in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a particular embodiment, the reference value for the percentage of progressive motile spermatozoa in a semen sample is 10%, 15%, 20%, 25%, 30%, 31%, 31.5%, 32%, 32.5%, 33%, 33.5%, 34%, 34.5%, 35%, 35.5%, 36%, 37%, 38%, 39%, 40%, 41%, 42%, 43%, 44%, 45%, 47%, 50%, 52%, 55%, 60%, 65%, 70%, 80%, 90%, 95%, preferably 30%, even more preferably 32%. In preferred embodiment, the reference value for the percentage of progressive motile spermatozoa in a semen sample is the LRL established by WHO in "WHO laboratory manual for the Examination and processing of human semen", 2010, fifth edition, for the percentage of progressive motile spermatozoa in a semen sample, which is 32%.

In another preferred embodiment, the reference value for the percentage of progressive motile spermatozoa in a semen sample of a male subject, is the percentage of progressive motile spermatozoa in a sample of semen of said male patient obtained before the treatment referred in the first aspect of the invention. In another preferred embodiment, it refers to the percentage of progressive motile spermatozoa in at least 1, at least 2, at least 3, at least 4, at least 5, at least 6, at least 7, at least 8, at least 9, at least 10, more preferably in at least 2 samples of semen of said male patient, obtained before the treatment referred in the first aspect of the invention has started. In a certain embodiment, if the reference value refers to the percentage of progressive motile spermatozoa in more than one sample obtained before the start of the treatment referred in the first aspect of the invention, said reference value corresponds to the mean of the values of the parameter "percentage of progressive motile spermatozoa" obtained in each of said samples. In a certain embodiment, said samples are each one obtained at a different time point, before the treatment referred in the first aspect of the invention has started.

The terms "after the treatment" and "before the treatment" have been previously defined.

In a particular embodiment of the first aspect of the invention, the percentage of morphologically normal spermatozoa in a sample of semen of the male patient after the treatment referred in the medical use of the invention is equal or above a reference value. Preferably, the percentage of morphologically normal spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has teratozoospermia and the percentage of morphologically normal spermatozoa in a sample of semen of said patient after the treatment referred in the medical use of the invention is equal or above a reference value. Preferably, the percentage of morphologically normal spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient is as defined in any of the embodiments of the first aspect of the invention before the treatment referred in said aspect of the invention, more preferably the patient has teratozoospermia before said treatment and the percentage of morphologically normal spermatozoa in a sample of semen of said male patient after said treatment is equal or above a reference value. Preferably, the percentage of morphologically normal spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

The expression "morphologically normal spermatozoa" has been provided above. Methods to determine the percentage of morphologically normal spermatozoa in a sample have been provided above in the definition of teratozoospermia.

The expression "percentage of morphologically normal spermatozoa in a semen sample above a reference value" as used herein, refers to any percentage of morphologically normal spermatozoa in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "percentage of morphologically normal spermatozoa in a semen sample equal to a reference value" as used herein, refers to any percentage of morphologically normal spermatozoa that is less than 10%, less than 5%, less than 4%, less than 3%, less than 2%, less than 1%, less than 0.5%, less than 0.1%, less than 0.05%, less than 0.01%, less than 0.001%, higher than its reference value, wherein 100% represents said reference value. It also refers to refers to any percentage of morphologically normal spermatozoa that is less than 10%, less than 5%, less than 4%, less than 3%, less than 2%, less than 1%, less than 0.5%, less than 0.1%, less than 0.05%, less than 0.01%, less than 0.001%, lower than its reference value, wherein 100% represents said reference value.

The expression "percentage of morphologically normal spermatozoa in a semen sample below a reference value", as used herein, refers to a percentage of morphologically normal spermatozoa in a semen sample which is at least 5%, at least 10%, at least 25%, at least 40%, at least 50%, at least 80%, at least 100%, preferably at least 25%, more preferably at least 50%, even more preferably at least 100% lower than its reference value, wherein 100% corresponds to said reference value.

In a particular embodiment the reference value for the percentage of morphologically normal spermatozoa in a sample is 0.5%, 1% 1.5%, 2%, 2.5%, 3%, 3.5%, 4%, 4.5%, 5%, 5.5%, 6%, 6.5%, 7%, 8%, 9%, 10%, 12%, 15%, 17%, 20%, 22%, 25%, 30%, 35%, 40%, preferably 4%. In a preferred embodiment, the reference value for the percentage of morphologically normal spermatozoa in a semen sample is the LRL established by the WHO in "WHO laboratory manual for the Examination and processing of human semen", 2010, fifth edition, which is 4%.

In another preferred embodiment, the reference value for the percentage of morphologically normal spermatozoa in a semen sample of a male subject, is the percentage of morphologically normal spermatozoa in a sample of semen of said male patient obtained before the treatment referred in the first aspect of the invention. In another preferred embodiment, it refers to the percentage of morphologically normal spermatozoa in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to the percentage of morphologically normal spermatozoa in more than one sample obtained before the start of the treatment referred in the first aspect of the invention, said reference value corresponds to the mean of the values of the parameter "percentage of morphologically normal spermatozoa in a semen sample" obtained in each of said samples. In another embodiment, said samples are each one obtained at a different time point, before the treatment referred in the first aspect of the invention has started.

The terms "after the treatment" and "before the treatment" have been previously defined.

In a particular embodiment of the first aspect of the invention, the volume of semen per ejaculate in a sample of semen of the male patient after the treatment referred in the medical use of the invention is equal or above a reference value. As indicate in the definition of "semen sample", a sample of semen of a male subject preferably comprises, or consists on, the semen of an ejaculate from said subject. Thus, as understood by a skilled person, the volume of semen per ejaculate in a semen sample is the volume of the semen sample. As also understood by a skilled person, the volume of semen per ejaculate in a semen sample is the volume of the ejaculate comprised in said sample, or on which the sample consists.

In case the sample of semen of a subject comprises more than one ejaculate of the subject, the volume of semen per ejaculate in the semen sample is the volume of one of said ejaculates. Said volume can be easily determine by a skilled person by dividing the volume of the sample by the number of ejaculates comprised in said sample, or in which the sample of semen consists.

Preferably, the volume of semen per ejaculate in a sample of semen of a male patient is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has hypospermia and the volume of semen per ejaculate in a sample of semen of said male patient after the treatment referred in the medical use of the invention is equal or above a reference value. Preferably, the volume of semen per ejaculate in a semen sample is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient of the medical use of the invention is as defined in any of the embodiments of the first aspect of the invention before the treatment referred in said aspect of the invention, more preferably the patient has hypospermia before said treatment, and the volume of semen per ejaculate in a sample of semen of said male patient after the treatment referred in the medical use of the invention is equal or above said reference value. Preferably, the volume of semen per ejaculate is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

Methods to determine the volume of semen in an ejaculate of a male patient have been provided above in the definition of hypospermia.

The expression "a volume of semen per ejaculate in a semen sample below a reference value" as used herein refers to a volume of semen per ejaculate which is at least 5%, at least 10%, at least 25%, at least 40%, at least 50%, at least 80%, at least 90%, at least 100%, lower than its reference value, wherein 100% corresponds to said reference value.

The expression "a volume of semen per ejaculate in a semen sample above a reference value" as used herein, refers to a volume of semen per ejaculate which is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "a volume of semen per ejaculate in a semen sample equal to a reference value" as used herein refers to a volume of semen per ejaculate that is equal, or substantially equal, to the reference value for the volume of semen of an ejaculate. Thus, the volume of semen per ejaculate is equal to its reference value if it is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, more preferably less than 1% higher than its reference value, wherein 100% represents said reference value. It is also equal to its reference value if it is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, more preferably less than 1% lower than its reference value, wherein 100% represents said reference value.

In another preferred embodiment, the reference value for the volume of semen per ejaculate is 5 ml, 4.5 ml, 4 ml, 3.5 ml, 3 ml, 2.5 ml, 2 ml, 1.5 ml, 1 ml, 0.5 ml, 0.25 ml, preferably 1.5 ml. In a preferred embodiment, the reference value corresponds to the LRL established by the WHO in "WHO laboratory manual for the Examination and processing of human semen", 2010, fifth edition and is 1.5 ml.

In another preferred embodiment, the reference value for the volume of semen per ejaculate in a semen sample is the volume of semen per ejaculate of said male subject obtained before the treatment referred in the first aspect of the invention. In another preferred embodiment, it refers to the volume of semen per ejaculate in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started.

In a certain embodiment, if the reference value refers to a volume of semen per ejaculate in more than one sample obtained before the start of the treatment referred in the first aspect of the invention, said reference value corresponds to the mean of the values of the parameter "volume of semen per ejaculate in a semen sample" obtained in each of said samples. In a certain embodiment, said samples are each one obtained at a different time point, before the treatment referred in the first aspect of the invention has started.

In another particular embodiment, the reference value for the volume of semen per ejaculate in a semen sample is lower than 0.25 ml, lower than 0.2 ml, lower than 0.1 ml, lower than 0.05 ml, lower than 0.01 ml, lower than 0.005 ml, preferably it is around 0 ml, more preferably it is 0 ml.

In another particular embodiment, since said reference value is the minimal one for the parameter "volume of semen per ejaculate in a semen sample", the expression "volume of semen per ejaculate in a semen sample below a reference value" refers to a volume of semen per ejaculate in a semen sample equal to said reference value. The expression "a volume of semen per ejaculate in a semen sample equal to a reference value" refers to a volume of semen per ejaculate in a semen sample that is, or coincides with, said reference value. In another particular embodiment, the expression "volume of semen per ejaculate in a semen sample above a reference value" refers to any value higher than said reference value, preferably it refers to an absolute value different from 0. In a preferred embodiment, it refers to a volume of semen per ejaculate in a semen sample of at least 0.001 ml, at least 0.005 ml, at least 0.01 ml, at least 0.1 ml, at least 0.2 ml, at least 0.5 ml, at least 1 ml, at least 1.5 ml, at least 1.75 ml, at least 2 ml, at least 2.5 ml, preferably at least 1.5 ml.

In another particular embodiment, the patient of the first aspect of the invention has aspermia. Methods to determine if a subject has aspermia have been provided in the definition of aspermia above. In another particular embodiment, all the embodiments where the term "hypospermia" is used also apply herein, by substituting the term "hypospermia" by "aspermia".

The terms "after the treatment" and "before the treatment" have been previously defined.

In a particular embodiment of the first aspect of the invention, the percentage of SDF in a sample of semen of the male patient after the treatment referred in the medical use of the invention is equal or below a reference value. In a preferred embodiment, the reference value for the percentage of SDF is any of those defined below for the parameter percentage of SDF. Preferably, the percentage of SDF is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has a disorder characterized by a percentage of SDF above a reference value and the percentage of SDF in a sample of semen of the male patient after the treatment referred in the medical use of the invention is equal or below a reference value. In a preferred embodiment, the reference value for the percentage of SDF is any of those defined below for the parameter percentage of SDF. Preferably, the percentage of SDF is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient of the medical use of the invention is as defined in any of the embodiments of the first aspect of the invention before the treatment referred in said aspect of the invention, more preferably the patient has a disorder characterized by a percentage of SDF above a reference value before said treatment and the percentage of SDF in a sample of semen of the male patient after said treatment is equal or below said reference value. In a preferred embodiment, the reference value for the percentage of SDF is any of those defined below for the parameter percentage of SDF. In another preferred embodiment, the percentage of SDF is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention. Methods to determine the percentage of SDF have been provided above in the definition of sperm DNA fragmentation.

The expression "a percentage of SDF in a semen sample above a reference value", as used herein, refers to a percentage of SDF in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "a percentage of SDF in a semen sample equal to a reference value", as used herein, refers to any percentage of SDF in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to a percentage of SDF that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "a percentage of SDF in a semen sample below a reference value", as used herein, refers to a percentage of SDF in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a preferred embodiment, any reference value referred above for a percentage of SDF in a semen sample is a percentage of SDF associated to poor or bad quality of a semen sample. Thus, said reference value is 15%, 16%, 17%, 18%, 19%, 20%, 21%, 22%, 23%, 24%, 25%, 26%, 27%, 28%, 29%, 30%, 31%, 23%, 33%, 34%, 35%, 36%, 37%, 38%, 39%, 40%, 42%, 45%, 47%, 50%, preferably 30%, more preferably 20%, even more preferably 18%, yet more preferably 16%, even yet more preferably 15%.

In another preferred embodiment, the reference value for the percentage of SDF in a semen sample of a male subject, is the percentage of SDF in a sample of semen of said male patient obtained before the treatment referred in the first aspect of the invention. In another preferred embodiment, it refers to the percentage of SDF in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to a percentage of SDF in more than one sample obtained before the start of the treatment referred in the first aspect of the invention, said reference value corresponds to the mean of the values of the parameter "percentage of SDF in a semen sample" obtained in each of said samples. In a certain embodiment, said samples are each one obtained at a different time point, before the treatment referred in the first aspect of the invention has started.

In another embodiment, the reference value for the percentage of SDF in a semen sample of a male subject, is the SDF in at least 1, at least 2, at least 3, at least 4, at least 5, at least 6, at least 7, at least 8, at least 9, at least 10, preferably in at least 2 samples of semen of a male subject considered healthy, preferably in a male subject considered fertile. In another embodiment, the reference value for the percentage of SDF in a semen sample of a male subject, is the SDF in at least 1, at least 2, at least 3, at least 4, at least 5, at least 6, at least 7, at least 8, at least 9, at least 10, preferably in at least 2 samples of semen of different male subjects considered healthy, preferably of different male subjects considered fertile. The definition of the term "fertile", or "fertility" is provided in the second aspect of the invention and applies to the present aspect of the invention.

The terms "after the treatment" and "before the treatment" have been previously defined.

In a particular embodiment of the first aspect of the invention, the level of 8-OH-dG in a sample of semen of the male patient after the treatment referred in the medical use of the invention is equal or below a reference value. In a preferred embodiment, the reference value for the level of 8-OH-dG in a semen sample is any of those defined below for the parameter level of 8-OH-dG in a semen sample. Preferably, the level of 8-OH-dG in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has a disorder characterized by a level of 8-OH-dG in semen above a reference value and the level of 8-OH-dG in a sample of semen of the male patient after the treatment referred in the medical use of the invention is equal or below a reference value. In a preferred embodiment, the reference value for the level of 8-OH-dG in a semen sample is any of those defined below for the parameter level of 8-OH-dG in semen. Preferably, the level of 8-OH-dG in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient of the medical use of the invention is as defined in any of the embodiments of the first aspect of the invention before the treatment referred in said aspect of the invention, more preferably the patient has a disorder characterized by a level of 8-OH-dG in semen above a reference value before said treatment and the level of 8-OH-dG in a sample of semen of the male patient after said treatment is equal or below said reference value. In a preferred embodiment, the reference value for level of 8-OH-dG in a semen sample is any of those defined below for the parameter level of 8-OH-dG in a semen sample. In another preferred embodiment, the level of 8-OH-dG in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention. Methods to determine the level of 8-OH-dG in semen or in a semen sample have been provided above in the definition of "level of 8-OH-dG in semen".

The expression "a level of 8-OH-dG in a semen sample above a reference value", as used herein, refers to a level of 8-OH-dG in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "a level of 8-OH-dG in a semen sample equal to a reference value", as used herein, refers to any percentage of SDF in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to a level of 8-OH-dG that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "a level of 8-OH-dG in a semen sample below a reference value", as used herein, refers to a level of 8-OH-dG in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a preferred embodiment, any reference value referred above for a level of 8-OH-dG in a semen sample is 300, 325, 350, 375, 400, 425, 450, 475, 500, 510, 515, 520, 525, 530, 535, 540, 545, 550, 551, 552, 553, 554, 555, 556, 557, 558, 559, 560, 562, 565, 567, 570, 575, 580, 585, 590, 595, 600, 625, 650, 675, 700, 750, 800, 850, 900 arbitrary units, preferably at least 552 arbitrary units, when the method is based in immunofluorescence followed by flow cytometry, as that described in Vorilhon et al., 2018, Human reproduction, 33(4): 553-562.

In another preferred embodiment, the reference value for a level of 8-OH-dG in a semen sample of a male subject, is the level of 8-OH-dG in a sample of semen of said male patient obtained before the treatment referred in the first aspect of the invention. In another preferred embodiment, it refers to the level of 8-OH-dG in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to a level of 8-OH-dG in more than one sample obtained before the start of the treatment referred in the first aspect of the invention, said reference value corresponds to the mean of the values of the parameter "level of 8-0H-dG in a semen sample" obtained in each of said samples. In a certain embodiment, said samples are each one obtained at a different time point, before the treatment referred in the first aspect of the invention has started.

In another embodiment, the reference value for the level of 8-OH-dG in a semen sample of a male subject, is the level of 8-OH-dG in at least 1, at least 2, at least 3, at least 4, at least 5, at least 6, at least 7, at least 8, at least 9, at least 10, preferably in at least 2 samples of semen of a male subject considered healthy, preferably of a male subject considered fertile. In another embodiment, the reference value for the level of 8-OH-dG in a semen sample of a male subject, is the level of 8-OH-dG in at least 1, at least 2, at least 3, at least 4, at least 5, at least 6, at least 7, at least 8, at least 9, at least 10, preferably in at least 2 samples of semen of different male subjects considered healthy, preferably of different male subjects considered fertile. The definition of the term "fertile", or "fertility" is provided in the second aspect of the invention and applies to the present aspect of the invention.

In another particular embodiment, as indicated above, the percentage of 8-OH-dG positive sperm cells in semen refers to the percentage of 8-OH-dG positive sperm cells in an ejaculate or in semen sample. Therefore, as understood by a skilled person, the reference value for the parameter "level of 8-OH-dG in semen", is interchangeable with the reference value for the parameter "level of 8-OH-dG in a semen sample". In an embodiment, the reference value for the parameter "level of 8-OH-dG in semen" is any of those provided above for the parameter "level of 8-OH-dG in a semen sample".

The terms "after the treatment" and "before the treatment" have been previously defined.

In a particular embodiment of the first aspect of the invention, the ratio $8\text{-OH-dG}/10^5$ dG in semen in a sample of semen of the male patient after the treatment referred in the medical use of the invention is equal or below a reference value. In a preferred embodiment, the reference value for the ratio $8\text{-OH-dG}/10^5$ dG in a semen sample is any of those defined below for the parameter ratio $8\text{-OH-dG}/10^5$ dG in a semen sample. Preferably, the ratio $8\text{-OH-dG}/10^5$ dG in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has a disorder characterized by a ratio $8\text{-OH-dG}/10^5$ dG in semen above a reference value and the ratio $8\text{-OH-dG}/10^5$ dG in a sample of semen of the male patient after the treatment referred in the medical use of the invention is equal or below a reference value. In a preferred embodiment, the reference value for the ratio $8\text{-OH-dG}/10^5$ dG in a semen sample is any of those defined below for the parameter ratio $8\text{-OH-dG}/10^5$ dG in semen. Preferably, the ratio $8\text{-OH-dG}/10^5$ dG in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient of the medical use of the invention is as defined in any of the embodiments of the first aspect of the invention before the treatment referred in said aspect of the invention, more preferably the patient has a disorder characterized by a ratio $8\text{-OH-dG}/10^5$ dG in semen above a reference value before said treatment and the ratio $8\text{-OH-dG}/10^5$ dG in a sample of semen of the male patient after said treatment is equal or below said reference value. In a preferred embodiment, the reference value for ratio $8\text{-OH-dG}/10^5$ dG in a semen sample is any of those defined below for the parameter ratio $8\text{-OH-dG}/10^5$ dG in a semen sample. In another preferred embodiment, the ratio $8\text{-OH-dG}/10^5$ dG in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention. Methods to determine the ratio $8\text{-OH-dG}/10^5$ dG in semen or in a semen sample have been provided above in the definition of "ratio $8\text{-OH-dG}/10^5$ dG in semen".

The expression "a ratio $8\text{-OH-dG}/10^5$ dG in a semen sample above a reference value", as used herein, refers to a ratio $8\text{-OH-dG}/10^5$ dG in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "a ratio 8-OH-dG/$10^5$ dG in a semen sample equal to a reference value", as used herein, refers to any percentage of SDF in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to a ratio 8-OH-dG/$10^5$ dG that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "a ratio 8-OH-dG/$10^5$ dG in a semen sample below a reference value", as used herein, refers to a ratio 8-OH-dG/$10^5$ dG in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a preferred embodiment, any reference value referred above for a ratio 8-OH-dG/$10^5$ dG in a semen sample is 1.0, 1.1, 1.2, 1.3, 1.4, 1.5, 1.6, 1.7, 1.8, 1.9, 2.0, 2.25, 2.5, 2.75, 3.0, 3.5, 4.0, 4.5, 5.0, 5.5, 6.0, 6.5, 7.0, 7.5, 8.0, 8.5, 9.0, 9.5, 10.0, 10.5, 11.0, 12, 13, 14, 15, 16, 17, 18, 19, 20, 30, 40, 50, 60, 80, 90, 100, preferably 1.5 8-0H-dG/$10^5$ dG.

In another preferred embodiment, the reference value for a ratio 8-OH-dG/$10^5$ dG in a semen sample of a male subject, is the ratio 8-OH-dG/$10^5$ dG in a sample of semen of said male patient obtained before the treatment referred in the first aspect of the invention. In another preferred embodiment, it refers to the ratio 8-OH-dG/$10^5$ dG in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to a ratio 8-OH-dG/$10^5$ dG in more than one sample obtained before the start of the treatment referred in the first aspect of the invention, said reference value corresponds to the mean of the values of the parameter "ratio 8-OH-dG/$10^5$ dG in a semen sample" obtained in each of said samples. In a certain embodiment, said samples are each one obtained at a different time point, before the treatment referred in the first aspect of the invention has started.

In another embodiment, the reference value for the ratio 8-OH-dG/$10^5$ dG in a semen sample of a male subject, is the ratio 8-OH-dG/$10^5$ dG in at least 1, at least 2, at least 3, at least 4, at least 5, at least 6, at least 7, at least 8, at least 9, at least 10, preferably in at least 2 samples of semen of a male subject considered healthy, preferably of a male subject considered fertile. In another embodiment, the reference value for the ratio 8-OH-dG/$10^5$ dG in a semen sample of a male subject, is the ratio 8-OH-dG/$10^5$ dG in at least 1, at least 2, at least 3, at least 4, at least 5, at least 6, at least 7, at least 8, at least 9, at least 10, preferably in at least 2 samples of semen of different male subjects considered healthy, preferably of different male subjects considered fertile. The definition of the term "fertile", or "fertility" is provided in the second aspect of the invention and applies to the present aspect of the invention.

In another particular embodiment, as indicated above, the ratio 8-OH-dG/$10^5$ dG in semen refers to the ratio 8-OHdG/$10^5$ dG in an ejaculate or in semen sample. Therefore, as understood by a skilled person, the reference value for the parameter "ratio 8-OH-dG/$10^5$ dG in semen", is interchangeable with the reference value for the parameter "ratio 8-OH-dG/$10^5$ dG in a semen sample". In an embodiment, the reference value for the parameter "ratio 8-OH-dG/$10^5$ dG in semen" is any of those provided above for the parameter "ratio 8-OH-dG/$10^5$ dG in a semen sample".

The terms "after the treatment" and "before the treatment" have been previously defined.

In a particular embodiment of the first aspect of the invention, the percentage of 8-OH-dG positive sperm cells in semen in a sample of semen of the male patient after the treatment referred in the medical use of the invention is equal or below a reference value. In a preferred embodiment, the reference value for the percentage of 8-OH-dG positive sperm cells in a semen sample is any of those defined below for the parameter percentage of 8-OH-dG positive sperm cells in a semen sample. Preferably, the percentage of 8-OH-dG positive sperm cells in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has a disorder characterized by a percentage of 8-OH-dG positive sperm cells in semen above a reference value and the percentage of 8-OH-dG positive sperm cells in a sample of semen of the male patient after the treatment referred in the medical use of the invention is equal or below a reference value. In a preferred embodiment, the reference value for the percentage of 8-OH-dG positive sperm cells in a semen sample is any of those defined below for the parameter percentage of 8-OH-dG positive sperm cells in semen. Preferably, the percentage of 8-OH-dG positive sperm cells in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient of the medical use of the invention is as defined in any of the embodiments of the first aspect of the invention before the treatment referred in said aspect of the invention, more preferably the patient has a disorder characterized by a percentage of 8-OH-dG positive sperm cells in semen above a reference value before said treatment and the percentage of 8-OH-dG positive sperm cells in a sample of semen of the male patient after said treatment is equal or below said reference value. In a preferred embodiment, the reference value for percentage of 8-OH-dG positive sperm cells in a semen sample is any of those defined below for the parameter percentage of 8-OH-dG positive sperm cells in a semen sample. In another preferred embodiment, the percentage of 8-OH-dG positive sperm cells in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention. Methods to determine the percentage of 8-OH-dG positive sperm cells in semen or in a semen sample have been provided above in the definition of "percentage of 8-OH-dG positive sperm cells in semen".

The expression "a percentage of 8-OH-dG positive sperm cells in a semen sample above a reference value", as used herein, refers to a percentage of 8-OH-dG positive sperm cells in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "a percentage of 8-OH-dG positive sperm cells in a semen sample equal to a reference value", as used herein, refers to any percentage of SDF in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to a percentage of 8-OH-dG positive sperm cells that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "a percentage of 8-OH-dG positive sperm cells in a semen sample below a reference value", as used herein, refers to a percentage of 8-OH-dG positive sperm cells in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a preferred embodiment, any reference value referred above for a percentage of 8-OH-dG positive sperm cells in a semen sample is 20%, 25%, 30%, 35%, 40%, 45%, 50%, 52%, 55%, 57%, 60%, 61%, 62%, 63%, 64%, 64.5%, 65%, 65.2%, 65.5%, 65.6%, 65.7%, 65.8%, 65.9%, 66%, 66.1%, 66.2%, 66.3%, 66.4%, 66.5%, 66.7%, 67%, 67.5%, 68%, 68.5%, 69%, 69.5%, 70%, 71%, 72%, 73%, 74%, 75% 77%, 80%, 82%, 875%, 87%, 90%, 95%, 97%, 98%, 99% of 8-OH-dG positive sperm cells with respect to the total number of spermatozoa in a semen sample, preferably of 65.8% of 8-OH-dG positive sperm cells with respect to the total number of spermatozoa in a semen sample In another preferred embodiment, the reference value for a percentage of 8-OH-dG positive sperm cells in a semen sample of a male subject, is the percentage of 8-OH-dG positive sperm cells in a sample of semen of said male patient obtained before the treatment referred in the first aspect of the invention. In another preferred embodiment, it refers to the percentage of 8-OH-dG positive sperm cells in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to a percentage of 8-OH-dG positive sperm cells in more than one sample obtained before the start of the treatment referred in the first aspect of the invention, said reference value corresponds to the mean of the values of the parameter "percentage of 8-OH-dG positive sperm cells in a semen sample" obtained in each of said samples. In a certain embodiment, said samples are each one obtained at a different time point, before the treatment referred in the first aspect of the invention has started.

In another embodiment, the reference value for the percentage of 8-OH-dG positive sperm cells in a semen sample of a male subject, is the percentage of 8-OH-dG positive sperm cells in at least 1, at least 2, at least 3, at least 4, at least 5, at least 6, at least 7, at least 8, at least 9, at least 10, preferably in at least 2 samples of semen of a male subject considered healthy, preferably of a male subject considered fertile. In another embodiment, the reference value for the percentage of 8-OH-dG positive sperm cells in a semen sample of a male subject, is the percentage of 8-OH-dG positive sperm cells in at least 1, at least 2, at least 3, at least 4, at least 5, at least 6, at least 7, at least 8, at least 9, at least 10, preferably in at least 2 samples of semen of different male subjects considered healthy, preferably of different male subjects considered fertile. The definition of the term "fertile", or "fertility" is provided in the second aspect of the invention and applies to the present aspect of the invention.

In another particular embodiment, as indicated above, the percentage of 8-OH-dG positive sperm cells in semen refers to the percentage of 8-OH-dG positive sperm cells in an ejaculate or in semen sample. Therefore, as understood by a skilled person, the reference value for the parameter "percentage of 8-OH-dG positive sperm cells in semen", is interchangeable with the reference value for the parameter "percentage of 8-OH-dG positive sperm cells in a semen sample". In an embodiment, the reference value for the parameter "percentage of 8-OH-dG positive sperm cells in semen" is any of those provided above for the parameter "percentage of 8-OH-dG positive sperm cells in a semen sample".

The terms "after the treatment" and "before the treatment" have been previously defined.

In a particular embodiment of the first aspect of the invention, the sORP in a sample of semen of the male patient after the treatment referred in the medical use of the invention is equal or below a reference value. In a preferred embodiment, the reference value for the sORP in a semen sample is any of those defined below for the parameter sORP in a semen sample. Preferably, the sORP in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has a disorder characterized by a sORP in semen above a reference value and the sORP in a sample of semen of the male patient after the treatment referred in the medical use of the invention is equal or below a reference value. In a preferred embodiment, the reference value for the sORP in a semen sample is any of those defined below for the parameter sORP in semen. Preferably, the sORP in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient of the medical use of the invention is as defined in any of the embodiments of the first aspect of the invention before the treatment referred in said aspect of the invention, preferably the patient has a disorder characterized by a sORP in semen above a reference value before said treatment and the sORP in a sample of semen of the male patient after said treatment is equal or below said reference value. In a preferred embodiment, the reference value for sORP in a semen sample is any of those defined below for the parameter sORP in a semen sample. In another preferred embodiment, the sORP in a semen sample is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention. Methods to determine the sORP in semen or in a semen sample have been provided above in the definition of "sORP in semen".

The expression "a sORP in a semen sample above a reference value", as used herein, refers to a sORP in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "a sORP in a semen sample equal to a reference value", as used herein, refers to any percentage of sORP in a semen sample that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to a level of sORP that is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "a sORP in a semen sample below a reference value", as used herein, refers to a sORP in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a preferred embodiment, any reference value referred above for a sORP in a semen sample is 0.5, 0.6, 0.7, 0.8, 0.9, 1.0, 1, 1.1, 1.2, 1.25, 0.27, 1.3, 10.31, 1.32, 1.33, 1.34, 1.35, 1.36, 1.37, 1.38, 1.39, 1.4, 1.41, 1.42, 1.43, 1.44, 1.45, 1.46, 1.47, 1.481, 1.49, 1.5, 1.51, 1.52, 1.53, 1.54, 1.55, 1.57, 1.6, 1.62, 1.65, 1.67, 1.7, 1.75, 1.8, 1.85, 1.9, 1.95, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.35, 5.6, 5.7, 5.8, 5.9, 6.0, 6.25, 6.5, 6.75, 7.0, 7.25, 7.5, 7.75, 8.0, 8.25, 8.5, 8.75, 9.0, 9.5, 10.0, 10.5, 11.0, 11.5, 12.0, 12.5, 13.0, 13.5, 14.0, 14.5, 15.0 mV/$10^6$ sperm/ml of semen, preferably 1.34 mV/$10^6$ sperm/ml of semen, more preferably 1.36 mV/$10^6$ sperm/ml of semen, even more preferably 1.48 mV/$10^6$ sperm/ml of semen.

In another preferred embodiment, the reference value for the sORP in a semen sample of a male subject, is the sORP in a sample of semen of said male patient obtained before the treatment referred in the first aspect of the invention. In another preferred embodiment, it refers to the sORP in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to a sORP in more than one sample obtained before the start of the treatment referred in the first aspect of the invention, said reference value corresponds to the mean of the values of the parameter "sORP in a semen sample" obtained in each of said samples. In a certain embodiment, said samples are each one obtained at a different time point, before the treatment referred in the first aspect of the invention has started.

In another embodiment, the reference value for the sORP in a semen sample of a male subject, is the sORP in at least 1, at least 2, at least 3, at least 4, at least 5, at least 6, at least 7, at least 8, at least 9, at least 10, preferably in at least 2 samples of semen of a male subject considered healthy, preferably of a male subject considered fertile. In another embodiment, the reference value for the sORP in a semen sample of a male subject, is the sORP in at least 1, at least 2, at least 3, at least 4, at least 5, at least 6, at least 7, at least 8, at least 9, at least 10, preferably in at least 2 samples of semen of different male subjects considered healthy, preferably of different male subjects considered fertile. The definition of the term "fertile", or "fertility" is provided in the second aspect of the invention and applies to the present aspect of the invention.

In another particular embodiment, as indicated above, the sORP in semen refers to the sORP in an ejaculate or in semen sample. Therefore, as understood by a skilled person, the reference value for the parameter "sORP in semen", is interchangeable with the reference value for the parameter "sORP in a semen sample". In an embodiment, the reference value for the parameter "sORP in semen" is any of those provided above for the parameter "sORP in a semen sample".

The terms "after the treatment" and "before the treatment" have been previously defined.

In a particular embodiment of the first aspect of the invention, the number of live spermatozoa in a sample of semen of the male patient after the treatment referred in the medical use of the invention is equal or above a reference value. Preferably, the percentage of live spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has necrozoospermia and the percentage of live spermatozoa in a sample of semen of said patient after the treatment referred in the medical use of the invention is equal or above a reference value. Preferably, the percentage of live spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

In a certain embodiment, the male patient is as defined in any of the embodiments of the first aspect of the invention before the treatment referred in said aspect of the invention, more preferably the patient has necrozoospermia before said treatment and the percentage of live spermatozoa in a sample of semen of said male patient after said treatment is equal or above a reference value. Preferably, the percentage of live spermatozoa is equal or above a reference value in at least 1, at least 2, at least 3, at least 4, at least 5, at least 6, at least 7, at least 8, at least 9, at least 10, at least 15, at least 20 samples, preferably in at least 2 samples of semen of the male patient, after the treatment referred in the medical use of the invention.

The expression "percentage of live spermatozoa" has been provided above. Methods to determine the percentage of live spermatozoa in a sample have been provided above in the definition of necrozoospermia.

The expression "percentage of live spermatozoa in a semen sample above a reference value" as used herein, refers to any percentage of live spermatozoa in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "percentage of live spermatozoa in a semen sample equal to a reference value" as used herein, refers to any percentage of live spermatozoa that is less than 10%, less than 5%, less than 4%, less than 3%, less than 2%, less than 1%, less than 0.5%, less than 0.1%, less than 0.05%, less than 0.01%, less than 0.001%, higher than its reference value, wherein 100% represents said reference value. It also refers to refers to any percentage of live spermatozoa that is less than 10%, less than 5%, less than 4%, less than 3%, less than 2%, less than 1%, less than 0.5%, less than 0.1%, less than 0.05%, less than 0.01%, less than 0.001%, lower than its reference value, wherein 100% represents said reference value.

The expression "percentage of live spermatozoa in a semen sample below a reference value", as used herein, refers to a percentage of live spermatozoa in a semen sample which is at least 5%, at least 10%, at least 25%, at least 40%, at least 50%, at least 80%, at least 100%, preferably at least 25%, more preferably at least 50%, even more preferably at least 100% lower than its reference value, wherein 100% corresponds to said reference value.

In a particular embodiment the reference value for the percentage of live spermatozoa in a sample is 30%, 35%, 40%, 45%, 50%, 51%, 52%, 53%, 54%, 55%, 56%, 57% 58%, 59%, 60%, 62%, 64%, 65%, 70%, 75%, preferably 58%. In a preferred embodiment, the reference value for the percentage of live spermatozoa in a semen sample is the LRL established by the WHO in "WHO laboratory manual for the Examination and processing of human semen", 2010, fifth edition, which is 58%.

In another preferred embodiment, the reference value for the percentage of live spermatozoa in a semen sample of a male subject, is the percentage of live spermatozoa in a sample of semen of said male patient obtained before the treatment referred in the first aspect of the invention. In another preferred embodiment, it refers to the percentage of live spermatozoa in at least 1, at least 2, at least 3, at least 4, at least 5, at least 6, at least 7, at least 8, at least 9, at least 10, preferably in at least 2 samples of semen of said male patient, obtained before the treatment referred in the first aspect of the invention has started. In a certain embodiment, if the reference value refers to the percentage of live spermatozoa in more than one sample obtained before the start of the treatment referred in the first aspect of the invention, said reference value corresponds to the mean of the values of the parameter "percentage of live spermatozoa in a semen sample" obtained in each of said samples. In another embodiment, said samples are each one obtained at a different time point, before the treatment referred in the first aspect of the invention has started.

The terms "after the treatment" and "before the treatment" have been previously defined.

In a particular embodiment of the first aspect of the invention, the concentration of leukocytes in a sample of semen of the male patient after the treatment referred in the medical use of the invention is equal or below a reference value. Preferably, the concentration of leukocytes is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a preferred embodiment, the male patient of the medical use of the invention is as defined in any of the embodiments of the first aspect of the invention, preferably the patient has leukospermia and the concentration of leukocytes in a sample of semen of said male patient after the treatment referred in the medical use of the invention is equal or below a reference value. Preferably, the concentration of leukocytes is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

In a certain embodiment, the male patient is as defined in any of the embodiments of the first aspect of the invention before the treatment referred in said aspect of the invention, preferably the patient has leukospermia before said treatment and the concentration of leukocytes in a sample of semen of said male patient after said treatment is equal or below a reference value. Preferably, the concentration of leukocytes is equal or below a reference value in at least 1, at least 2, at least 3, at least 4, at least 5, at least 6, at least 7, at least 8, at least 9, at least 10, at least 15, at least 20 samples, preferably in at least 2 samples of semen of the male patient after the treatment referred in the medical use of the invention.

Methods to determine the concentration of leukocytes in a semen sample have been provided above in the definition of leukospermia.

The expression "concentration of leukocytes in a semen sample above a reference value" as used herein, refers to any concentration of leukocytes in a semen sample that is at least 5%, at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than said reference value, wherein 100% corresponds to said reference value.

The expression "concentration of leukocytes in a semen sample equal to a reference value", as used herein, refers to any concentration of leukocytes in semen sample which is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% higher than its reference value, wherein 100% represents said reference value. It also refers to any concentration of leukocytes in semen sample which is less than 10%, less than 5%, less than 4%, less than 3%, less than 2%, less than 1%, less than 0.5%, less than 0.1%, less than 0.05%, less than 0.01%, less than 0.001%, preferably less than 5%, more preferably less than 2%, yet more preferably less than 1% lower than its reference value, wherein 100% represents said reference value.

The expression "concentration of leukocytes in a semen sample below a reference value", as used herein, refers to a concentration of leukocytes in a semen sample which is at least 5%, at least 10%, at least 25%, at least 40%, at least 50%, at least 80%, at least 90%, at least 100%, preferably at least 25%, more preferably at least 50%, even more preferably at least 90% lower than its reference value, wherein 100% corresponds to said reference value.

In a particular embodiment, the reference value for the concentration of leukocytes in a semen sample is $1*10^5$, $2.5*10^5$, $5*10^5$, $7.5*10^5$, $1*10^6$, $1.25*10^6$, $1.5*10^6$, $1.75*10^6$, $2*10^6$, $1.25*10^6$, $2.5*10^6$, $2.75*10^6$, $3*10^6$, $5*10^6$ leukocytes per ml of semen, preferably $1*10^6$ leukocytes per ml of semen. In a preferred embodiment, the reference value for the concentration of leukocytes in a semen sample corresponds to the LRL established by the WHO in "WHO laboratory manual for the Examination and processing of human semen", 2010, fifth edition for the total concentration of leukocytes per ml of semen which is $1*10^6$ leukocytes per ml of semen, or $1.0*10^6$ peroxidase-positive leukocytes per ml of semen.

In another preferred embodiment, the reference value for the concentration of leukocytes in a semen sample of a male subject is the concentration of leukocytes in a sample of semen of said male patient obtained before the treatment referred in the first aspect of the invention. In another preferred embodiment, it refers to the concentration of leukocytes in at least 1, at least 2, at least 3, at least 4, at least 5, at least 6, at least 7, at least 8, at least 9, at least 10, more preferably in at least 2 samples of semen of said male patient, obtained before the treatment referred in the first aspect of the invention has started. In a certain embodiment, if the reference value refers to the concentration of leukocytes in more than one sample obtained before the start of the treatment referred in the first aspect of the invention, said reference value corresponds to the mean of the values of the parameter "concentration of leukocytes" obtained in each of said samples. In a certain embodiment, said samples are each one obtained at a different time point, before the treatment referred in the first aspect of the invention has started.

In a particular embodiment, the type of leukocytes analyzed in a semen sample are polymorphonuclear leukocytes. In this case, the parameter analyzed is the concentration of polymorphonuclear leukocytes, instead of the concentration of leukocytes in a semen sample. In this case, all the embodiments provided above where the expression "concentration of leukocytes in a semen sample" is used also apply, by substituting the expression "concentration of leukocytes" by "concentration of polymorphonuclear leukocytes". The reference value for the concentration of polymorphonuclear leukocytes is $0.5*10^5$, $1*10^5$, $2.5*10^5$, $5*10^5$, $7.5*10^5$, $1*10^6$, $1.25*10^6$, $1.5*10^6$, $1.75*10^6$, $2*10^6$, $1.25*10^6$, $2.5*10^6$, $2.75*10^6$, $3*10^6$, $5*10^6$ polymorphonuclear leukocytes per ml of semen, preferably $5*10^5$ polymorphonuclear leukocytes per ml of semen.

The terms "after the treatment" and "before the treatment" have been previously defined.

In a preferred embodiment, the treatment referred in the first aspect of the invention comprises the administration of the biomass, the protein extract or the pharmaceutical composition of the first aspect of the invention for a certain period of time, at a certain frequency and with a certain dose each time during this period of time.

In a particular embodiment, said period of time is of at least 7 days, at least 15 days, at least 20 days, at least 25 days, at least 30 days, at least 35 days, at least 40 days, at least 50 days, at least 60 days, at least 65 days, at least 70 days, at least 75 days, at least 80 days, at least 85 days, at least 90 days, at least 95 days, at least 100 days, at least 4 months, at least 5 months, at least 6 months, at least 7 months, at least 8 months, at least 9 months, at least 10 months, at least 11 months, at least 1 year, at least 1.5 years, at least 2 years, at least 3 years, at least 5 years, at least 10 years, preferably at least 30 days (i.e. 1 month), more preferably of at least 65 days, even more preferably of at least 70 days, yet more preferably of at least 90 days. Thus, in a particular embodiment, the treatment referred in the medical use of the invention comprises the administration of the biomass, the protein extract or the pharmaceutical composition referred in the first aspect of the invention for at least 30 days (i.e. 1 month). In another particular embodiment, the treatment referred in the medical use of the invention comprises the administration of the biomass, the protein extract or the pharmaceutical composition referred in the first aspect of the invention for at least 65 days. In another particular embodiment, the treatment referred in the medical use of the invention comprises the administration of the biomass, the protein extract or the pharmaceutical composition referred in the first aspect of the invention for at least 70 days. In another particular embodiment, the treatment referred in the medical use of the invention comprises the administration of the biomass, the protein extract or the pharmaceutical composition referred in the first aspect of the invention for at least 90 days (i.e. 3 months). In another particular embodiment, said frequency is at least once, at least twice, at least 3 times, at least 4 times, at least 5 times per day, preferably during every day along said period of time. In another particular embodiment, said frequency is at least once, at least twice, at least 3 times, at least 4 times, at least 5 times per day every 2 days, preferably along said period of time. In another particular embodiment, said frequency is at least once, at least twice, at least 3 times, at least 4 times, at least 5 times per day every 3 days, preferably along said period of time. In another particular embodiment, said frequency is at least once, at least twice, at least 3 times, at least 4 times, at least 5 times per day every 4 days, preferably along said period of time. In another particular embodiment, said frequency is at least once, at least twice, at least 3 times, at least 4 times, at least 5 times per day every 5 days, preferably along said period of time. In another particular embodiment, said frequency if at least once, at least twice, at least 3 times, at least 4 times, at least 5 times per day every 6 days, preferably along said period of time. In another particular embodiment, said frequency is at least once, at least twice, at least 3 times, at least 4 times, at least 5 times per day every 7 days, preferably during said period of time. In another particular embodiment, said frequency is at least once, at least twice, at least 3 times, at least 4 times, at least 5 times per day every 10 days, preferably during said period of time. In another particular embodiment, said frequency is at least once, at least twice, at least 3 times, at least 4 times, at least 5 times per day every 2 weeks, preferably during said period of time. In a preferred embodiment, said frequency is once a day during said period of time. In a more preferred embodiment, said frequency is once a day, preferably every day, during the whole period of the treatment, which is any of the periods indicated above.

In a particular embodiment, when the treatment referred in the first aspect of the invention comprises the adminis- tration of biomass of *T. chuii* and said biomass is a dehy- drated biomass, the dose at which said biomass is adminis- tered is of 1 mg, 2 mg, 3 mg, 4 mg, 5 mg, 10 mg, 15 mg, 20 mg, 25 mg, 30 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.5 g, 2 g, 2.5 g, 3 g, 3.5 g, 4 g, 4.5 g, 5 g of dehydrated biomass. In another preferred embodiment, the treatment referred in the first aspect of the invention com- prises administering 10-500 mg of dehydrated biomass, more preferably 500 mg, even more preferably 250 mg of dehydrated biomass of *T. chuii*. In a preferred embodiment, the treatment of the first aspect of the invention comprises administering 10-500 mg of dehydrated biomass per day, preferably 250 mg of dehydrated biomass per day.

In another particular embodiment, when said biomass is a fresh biomass, said dose is of 2.5 mg, 3 mg, 4 mg, 5 mg, 6 mg, 8 mg, 9 mg, 10 mg, 11 mg, 12 mg, 13 mg, 14 mg, 15 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 290 mg, 300 mg, 350 mg, 400 mg, 450 mg, 500 mg, 550 mg, 600 mg, 625 mg, 650 mg, 700 mg, 750 mg, 800 mg, 850 mg, 900 mg, 950 mg, 1 g, 1.25 g, 1.5 g, 1.7 g, 2 g, 2.1 g, 2.2 g, 2.3 g, 2.4 g, 2.5 g, 2.6 g, 2.7 g, 2.8 g, 2.9 g, 3 g, 3.25 g, 3.5 g, 3.75 g, 4 g, 4.5 g, 5 g, of fresh biomass.

In a preferred embodiment, the treatment referred in the first aspect of the invention comprises administering 30 mg-4 g of fresh biomass, preferably 4 g, more preferably 3 g, even more preferably 40 mg, yet more preferably 30 mg of fresh biomass. In another preferred embodiment, the treatment referred in the first aspect of the invention com- prises administering 30 mg-4 g of fresh biomass per day, preferably 4 g, more preferably 3 g, even more preferably 40 mg, yet more preferably 30 mg of fresh biomass per day.

In a particular embodiment, the treatment referred in the first aspect of the invention comprises the administration of a protein extract of *T. chuii* as defined herein, and the dose for its administration is of 0.2 mg, 0.4 mg, 0.5 mg, 0.6 mg, 0.8 mg, 1 mg, 1.2 mg, 1.4 mg, 1.6 mg, 1.8 mg, 2 mg, 3 mg, 4 mg, 5 mg, 6 mg, 8 mg, 10 mg, 12 mg, 15 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 300 mg, 400 mg, 500 mg, 600 mg, 700 mg, 800 mg, 900 mg, 1 g, 1.5 g, 2 g of protein extract of T.

In another preferred embodiment, the treatment referred in the first aspect of the invention comprises administering 4-200 mg of protein extract, more preferably 200 mg, even more preferably 100 mg of protein extract of *T. chuii*. In a preferred embodiment, the treatment of the first aspect of the invention comprises administering 4-200 mg of protein extract per day, preferably 10 mg of protein extract per day.

In a particular embodiment, when the treatment referred in the first aspect of the invention comprises the adminis- tration of a pharmaceutical composition comprising a fresh biomass of *T. chuii*, it is administered in a dose that results in the administration of said fresh biomass in any of the amounts indicated above for the fresh biomass. In another particular embodiment, when said pharmaceutical compo- sition comprises the dehydrated biomass of *T. chuii*, it is administered in a dose that results in the administration of said dehydrated biomass in any of the amounts indicated above for the dehydrated biomass. In another particular embodiment, when the treatment referred in the first aspect of the invention comprises the administration of a pharma- ceutical composition comprising a protein extract of *T. chuii*, it is administered in a dose that results in the administration of said protein extract in any of the amounts indicated above for the protein extract of *T. chuii*.

In a preferred embodiment, the biomass, the protein extract or the pharmaceutical composition referred in the medical use of the invention is in the form of tablets, capsules, liquid suspensions, dried powder, or a wet com- position. Thus, in a preferred embodiment, the biomass, the protein extract or the pharmaceutical composition referred in the medical use of the invention is administered in any of said forms.

II—Method of the Invention

In a second aspect, the invention relates to a method for increasing the quality of the semen of a male subject having normozoospermia, not having hypospermia, and not having a disorder characterized by a percentage of Sperm DNA Fragmentation (SDF) above a reference value, comprising treating the subject by administering a biomass of *T. chuii* or a protein extract of *T. chuii*. In a particular embodiment, the male subject of the second aspect of the invention does not have a disorder characterized by a level of 8-OH-dG, a ratio of $8OH\text{-}dG/10^5$ dG or a percentage of 8-OH-dG positive sperm cells, in semen above a reference value. In another particular embodiment, the male subject of the second aspect of the invention does not have a disorder character- ized by a sORP in semen above a reference value. In a particular embodiment, the male subject of the second aspect of the invention does not have aspermia. In another particular embodiment, the male subject of the second aspect of the invention does not have leukospermia. In another particular embodiment, the male subject of the second aspect of the invention does not have necrozoosper- mia. In another particular embodiment, the male subject of the second aspect of the invention has normozoospermia, does not have hypospermia, does not have a disorder char- acterized by a percentage of SDF above a reference value, does not have a disorder characterized by a level of 8-OH- dG, a ratio of $8OH\text{-}dG/10^5$ dG or a percentage of 8-OH-dG positive sperm cells in semen above a reference value, does not have a disorder characterized by a sORP in semen above a reference value, does not have aspermia, does not have leukospermia, and does not have necrozoospermia. In a particular embodiment, the male subject of the second aspect of the invention does not suffer from infertility.

In a particular embodiment, the method of the second aspect is a non-therapeutic method.

The expression "quality of the semen of a male subject", as used herein, refers to the characterization of the semen of a male subject with respect to how excellent or good it is to accomplish fertilization. The quality of the semen is deter- mined by measuring different semen parameters. Non-lim- iting examples of said parameters include: the total number of spermatozoa in a semen sample, the concentration of spermatozoa in a semen sample, the volume of semen obtained from an ejaculate, the percentage of morphologi- cally normal spermatozoa in a semen sample, the percentage of progressively motile spermatozoa in a semen sample, the percentage of live spermatozoa in a semen sample, the concentration of leukocytes in a semen sample, the percent- age of SDF, the level of 8-OH-dG, the ratio of $8OH\text{-}dG/10^5$ dG or the percentage of 8-OH-dG positive sperm cells in a semen sample or the sORP in a semen sample.

The definitions of "aspermia", "hypospermia", "leukospermia", "necrozoospermia", "morphologically normal spermatozoa", "progressively motile spermatozoa", "percentage of SDF", "level of 8-OH-dG in semen", "the ratio of 8OH-dG/$10^5$ dG in semen", "the percentage of 8-OH-dG positive sperm cells in semen" as well as "the sORP in semen" have been provided in the first aspect of the invention and apply to the second aspect of the invention. Methods to determine the total number of spermatozoa in a semen sample, the concentration of spermatozoa in a semen sample, the volume of semen obtained from an ejaculate, the percentage of morphologically normal spermatozoa in a semen sample, the percentage of progressively motile spermatozoa in a semen sample, the percentage of live spermatozoa in a semen sample, the concentration of leukocytes in a semen sample, the percentage of SDF, the level of 8-OH-dG, the ratio of 8OH-dG/$10^5$ dG or the percentage of 8-OH-dG positive sperm cells in a semen sample or the sORP in a semen sample have also been provided in the first aspect of the invention and apply to the second aspect of the invention.

The expression "increase the quality of the semen of a male subject", or "increasing the quality of the semen of a male subject", refers to the increase in the capacity of the semen of a male subject to accomplish fertilization as compared to a control semen sample from said male subject. Said increase can be determined by measuring at least one semen parameter in a semen sample from said male subject, wherein if at least one semen parameter in said semen sample shows an improvement with respect to the control semen sample, then it is considered that the quality of the semen of the male subject has increased, i.e. the capacity of the semen of the male subject to accomplish fertilization has increased. Therefore, "a method for increasing the quality of the semen of a male subject", as used herein, refers to a method for improving at least one semen parameter in the semen of a male subject with respect to a control sample.

In a preferred embodiment, at least 1, at least 2, at least 3, at least 4, at least 5, at least 6, at least 7, at least 8, at least 9, at least 10 samples, preferably at least 2 semen samples of said male subject have to show an improvement in at least one semen parameter with respect to a control sample for the quality of the semen of said male subject to be considered to have increased. Therefore, in a preferred embodiment, a method for increasing the quality of the semen of a male subject, as used herein, refers to a method for improving at least one semen parameter in at least 1, at least 2, at least 3, at least 4, at least 5, at least 6, at least 7, at least 8, at least 9, at least 10 semen samples, preferably in at least 2 semen samples of said male subject, with respect to a control sample.

A semen parameter in a semen sample of a male subject is considered to have improved with respect to a control semen sample if the semen parameter is the total number of spermatozoa in a semen sample, the volume of semen obtained from an ejaculate, the percentage of morphologically normal spermatozoa in a semen sample, the percentage of progressively motile spermatozoa in a semen sample or the percentage of live spermatozoa in a semen sample and the value of said parameter is higher in the semen sample of the male subject than the value of said parameter in the control semen sample. A semen parameter in a semen sample of a male subject is also considered to have improved with respect to a control semen sample if the parameter is the concentration of leukocytes in a semen sample, the percentage of SDF in a semen sample, the level of 8OH-dG in a semen sample, the ratio of 8OH-dG/$10^5$ dG in a semen sample, the percentage of 8-OH-dG positive sperm cells in a semen sample or the sORP in a semen sample and the value of said parameter is lower in the semen sample of the male subject than the value of said parameter in the control sample.

In a preferred embodiment the expression "the value of said parameter is higher in the semen sample of the male subject than the value of said parameter in the control semen sample" as used herein, refers to a value of said parameter in the semen sample of the male subject, at least 10%, at least 25%, at least 40%, at least 50%, at least 80%, at least 100%, at least 150%, at least 200%, at least 300%, at least 400%, at least 500%, at least 600%, at least 800%, or at least 1000% higher than in the control semen sample. In a preferred embodiment, said expression refers to a value of the parameter in the semen sample of the male subject at least 25% higher than the value of the parameter in the control sample. In another preferred embodiment, said expression refers to a value of the parameter in the semen sample of the male subject at least 50% higher than the value of the parameter in the control sample. In another preferred embodiment, said expression refers to a value of the parameter in the semen sample of the male subject at least 100% higher than the value of the parameter in the control sample. In another preferred embodiment, said expression refers to a value of the parameter in the semen sample of the male subject at least 150% higher than the value of the parameter in the control sample. In another preferred embodiment, said expression refers to a value of the parameter in the semen sample of the male subject at least 200% higher than the value of the parameter in the control sample.

In another preferred embodiment, the expression "the value of said parameter is lower in the semen sample of the male subject than the value of said parameter in the control sample" as used herein, refers to a value of said parameter in the semen sample of the male subject at least 5%, at least 10%, at least 25%, at least 40%, at least 50%, at least 80%, at least 90%, at least 100% lower than in the control sample. In a preferred embodiment, said expression refers to a value of the parameter in the semen sample of the male subject at least 25% lower than the value of said parameter in the control sample. In a preferred embodiment, said expression refers to a value of the parameter in the semen sample of the male subject at least 50% lower than the value of said parameter in the control sample. In a preferred embodiment, said expression refers to a value of the parameter in the semen sample of the male subject at least 80% lower than the value of said parameter in the control sample. In a preferred embodiment, said expression refers to a value of the parameter in the semen sample of the male subject at least 90% lower than the value of said parameter in the control sample. In a preferred embodiment, said expression refers to a value of the parameter in the semen sample of the male subject at least 100% lower than the value of said parameter in the control sample.

In a certain embodiment, when the control sample is a set of samples as indicated below, the value of the semen parameter in the control sample is the mean of the values of said parameter in each of the samples of the set.

In a preferred embodiment, the control sample is a semen sample from the male subject of the method of the invention, obtained at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 1 day, at least 2 days, at least 3 days, at least 5 days, at least 6 days, at least 1 week, at least 2 weeks, at least 3 weeks, at least 1 month, at least 2 months, at least 3 months, at least 6 months, at least 9 months, at least 1 year, at least 2 years, at least 3 years, at least 4 years, at least 5 years, before the method of the invention is carried out. In a further preferred embodiment, the control sample is a semen sample from the male subject of the method of the invention obtained preferably at least 1 month, more preferably at least 1 week, even more preferably at least 1 day, yet more preferably at least 1 hour before the method of the invention is carried out.

In a certain embodiment, the control sample is a set of semen samples, preferably 2, 3, 4, or 5, more preferably 2 semen samples from the male subject of the method of the invention. In a preferred embodiment they are obtained at different time points, selected from those indicated above for the control sample. In this case, said samples are obtained as described in any of the embodiments provided in the first aspect of the invention for obtaining the semen samples.

In a preferred embodiment, the control sample is from a subject having normozoospermia. In another preferred embodiment, the control sample is from a subject not having a disorder associated with a percentage of SDF higher than a reference value, that is, the control sample shows a percentage of SDF lower than a reference value. In another particular embodiment, the control sample is from a subject not having hypospermia. In a particular embodiment, when the control sample is a set of semen samples as indicated above, each of said samples are from a male subject having normozoospermia, not having hypospermia, and/or not having a disorder associated with a percentage of SDF higher than a reference value, that is, the control samples show a percentage of SDF lower than a reference value.

In another embodiment, the control sample is from a subject not having a disorder associated with a level of 8-OH-dG, a ratio of 8OH-dG/$10^5$ dG or a percentage of 8-OH-dG positive sperm cells in semen above a reference value, that is, the control sample shows a level of 8-OH-dG, a ratio of 8OH-dG/$10^5$ dG ora percentage of 8-OH-dG positive sperm cells lower than a reference value. In another particular embodiment, the control sample is from a subject not having a disorder associated with a sORP in semen above a reference value, that is, the control sample shows a sORP lower than a reference value. In another particular embodiment, the control sample is from a subject not having necrozoospermia. In another particular embodiment the control sample is from a subject not having leukospermia. As understood by a skilled person, the control sample is from a subject not having aspermia.

The term "normozoospermia", as used herein, refers to a condition characterized in that the total number of spermatozoa and/or the concentration of spermatozoa, the percentage of PR and the percentage of morphologically normal spermatozoa in the semen of a male subject is equal to or above the corresponding LRL. The WHO establishes in "WHO laboratory manual for the Examination and processing of human semen", 2010, fifth edition that the LRL for:

total sperm number is 39*$10^6$ per ejaculate,
   sperm concentration is 15*$10^6$ per ml,
   percentage of progressively motile spermatozoa is 32%,
   percentage of morphologically normal spermatozoa is 4%.

In a preferred embodiment, a subject has normozoospermia when at least 1, at least 2, at least 3, at least 4, at least 5, at least 6, at least 7, at least 8, at least 9, at least 10, preferably at least 2 semen samples of said male subject show a total number of spermatozoa and/or a concentration of spermatozoa, a percentage of PR and a percentage of morphologically normal spermatozoa equal or above a corresponding reference value. In another preferred embodiment, the reference value for the total number of spermatozoa and/or a concentration of spermatozoa, the percentage of PR and the percentage of morphologically normal spermatozoa is any of those provided for each of said parameters in the first aspect of the invention.

Methods for determining the total number of spermatozoa, the concentration of spermatozoa, the percentage of PR and the percentage of morphologically normal spermatozoa in the semen of a male patient, or in a semen sample, are provided in the first aspect of the invention in the definition of "oligozoospermia", "asthenospermia" and "teratozoospermia", and apply to the second aspect of the invention.

In a preferred embodiment, the reference value of the percentage of SDF referred in the second aspect of the invention is any of the reference values provided for said parameter in the first aspect of the invention. Methods for determining the percentage of SDF in the semen of a male patient, or in a semen sample, are provided in the first aspect of the invention in the definition of "percentage of SDF".

In another preferred embodiment, the reference value for the level of 8-OH-dG, the ratio of 8OH-dG/$10^5$ dG or the percentage of 8-OH-dG positive sperm cells, in semen or in a semen sample, referred in the second aspect of the invention, is any of the reference values provided for said parameter in the first aspect of the invention. Methods for determining the level of 8-OH-dG, the ratio of 8OH-dG/$10^5$ dG or the percentage of 8-OH-dG positive sperm cells in the semen of a male patient, or in a semen sample, are provided in the first aspect of the invention in the definition "level of 8-OH-dG in semen", "ratio of 8OH-dG/$10^5$ dG in semen", or "percentage of 8-OH-dG positive sperm cells in semen", respectively.

In a preferred embodiment, the reference value of the sORP referred in the second aspect of the invention is any of the reference values provided for said parameter in the first aspect of the invention. Methods for determining the sORP in the semen of a male patient, or in a semen sample, are provided in the first aspect of the invention in relation with the definition of "sORP in semen".

In another preferred embodiment, the male subject of the second aspect of the invention is fertile.

The term "fertility" as used herein refers to a condition of the reproductive system defined by the capacity to achieve a clinical pregnancy within 12 months or less of regular unprotected sexual intercourse. The expression "male fertility" as used herein refers to fertility of a male subject. As understood by a person skilled in the art, a male shown to be fertile is preferably characterized by not showing an alteration leading to infertility, in particular, a deficiency in any semen parameter. Said semen parameters include the total number of spermatozoa, the concentration of spermatozoa, the volume of semen from an ejaculate, the percentage of morphologically normal spermatozoa, the percentage of progressively motile spermatozoa, the percentage of live spermatozoa, the concentration of leukocytes, the percentage of SDF, the level of 8-OH-dG, the ratio of 8OH-dG/$10^5$ dG or the percentage of 8-OH-dG positive sperm cells, or the level of sORP. As a person skilled in the art will understand, a semen sample of a male subject considered to be fertile, preferably shows a number and/or concentration of spermatozoa, a volume of semen per ejaculate, a percentage of morphologically normal spermatozoa, a percentage of progressively motile spermatozoa and a percentage of live spermatozoa equal to or higher than a reference value. In addition, a semen sample of a male subject considered to be fertile, preferably shows a concentration of leukocytes, a percentage of SDF, a level of 8-OH-dG, a ratio of 8OH-dG/$10^5$ dG, a percentage of 8-OH-dG positive sperm cells and a level of sORP equal or lower than a reference value. Therefore, in a particular embodiment, a semen sample of the male subject of the method of the invention shows a total number of spermatozoa, a concentration of spermatozoa, a volume of semen per ejaculate, a percentage of morphologically normal spermatozoa, a percentage of progressively motile spermatozoa and a percentage of live spermatozoa equal to or higher than a reference value. In addition, a semen sample of a male subject considered to be fertile, preferably shows a concentration of leukocytes, a percentage of SDF, a level of 8-OH-dG, a ratio of 8OH-dG/$10^5$ dG, a percentage of 8-OH-dG positive sperm cells and a level of sORP equal or lower than a reference value.

In a preferred embodiment, when a male subject is fertile, at least 1, at least 2, at least 3, at least 4, at least 5, at least 6, at least 7, at least 8, at least 9, at least 10, preferably at least 2 samples of semen of said subject show a total number of spermatozoa, a concentration of spermatozoa, a volume of semen per ejaculate, a percentage of morphologically normal spermatozoa, a percentage of progressively motile spermatozoa and a percentage of live spermatozoa equal to or higher than a reference value, and a concentration of leukocytes, a percentage of SDF, a level of 8-OH-dG, a ratio of 8OH-dG/$10^5$ dG, a percentage of 8-OH-dG positive sperm cells and a level of sORP equal to or lower than a reference value.

The expressions "a total number of spermatozoa in a semen sample below a reference value", "a concentration of spermatozoa in a semen sample below a reference value", "a percentage of morphologically normal spermatozoa in a semen sample below a reference value", "a percentage of progressively motile spermatozoa in a semen sample below a reference value", "a volume of semen per ejaculate in a semen sample below a reference value", "a percentage of SDF in a semen sample above a reference value", "a level of 8-OH-dG in a semen sample above a reference value", "ratio of 8OH-dG/$10^5$ dG in a semen sample above a reference value", "percentage of 8-OH-dG positive sperm cells in a semen sample above a reference value", "sORP above a reference value", "concentration of leukocytes in a semen sample above a reference value", and "percentage of live spermatozoa below a reference value in a semen sample" have been defined and described in different embodiments above in the first aspect of the invention and said definitions and embodiments apply to the second aspect of the invention.

The expression "a total number of spermatozoa in a semen sample equal to a reference value", "a concentration of spermatozoa in a semen sample equal to a reference value", "a percentage of morphologically normal spermatozoa in a semen sample equal to a reference value", "a percentage of progressively motile spermatozoa in a semen sample equal to a reference value", "a volume of semen per ejaculate in a semen sample equal to a reference value", "a percentage of SDF in a semen sample equal to a reference value", "a level of 8-OH-dG in a semen sample equal to a reference value", "ratio of 8OH-dG/$10^5$ dG in a semen sample equal to a reference value", "percentage of 8-OH-dG positive sperm cells in a semen sample equal to a reference value", "sORP equal to a reference value", "concentration of leukocytes in a semen sample equal to a reference value" and "percentage of live spermatozoa in a semen sample equal to a reference value" have been defined and described in different embodiments above in the first aspect of the invention and said definitions and embodiments apply to the second aspect of the invention.

The expression "a total number of spermatozoa in a semen sample above a reference value", "a concentration of spermatozoa in a semen sample above a reference value", "a percentage of morphologically normal spermatozoa in a semen sample above a reference value", "a percentage of progressively motile spermatozoa in a semen sample above a reference value", "a volume of semen per ejaculate in a semen sample above a reference value" "a percentage of SDF in a semen sample below a reference value", "a level of 8-OH-dG in a semen sample below a reference value", "ratio of 8OH-dG/$10^5$ dG in a semen sample below a reference value", "percentage of 8-OH-dG positive sperm cells in a semen sample below a reference value", "sORP below a reference value" "concentration of leukocytes in a semen sample below a reference value" and "percentage of live spermatozoa in a semen sample above a reference value" have been defined and described in different embodiments above in the first aspect of the invention and said definitions and embodiments apply to the second aspect of the invention.

In a preferred embodiment, the reference value for the total number of spermatozoa in a semen sample, for the concentration of spermatozoa in a semen sample, for the percentage of morphologically normal spermatozoa in a semen sample, for the percentage of progressively motile spermatozoa in a semen sample, for the volume of semen per ejaculate in a semen sample, for the percentage of SDF in a semen sample, for the level of 8-OH-dG in a semen sample, for the ratio of 8OH-dG/$10^5$ dG in a semen sample, for the percentage of 8-OH-dG positive sperm cells in a semen sample, for the level of sORP in a semen sample, for the concentration of leukocytes in a semen sample, and for the percentage of live spermatozoa in a semen sample are those specified in the first aspect of the invention for the corresponding parameter.

The term "treating", as used in the second aspect of the invention, refers to the administration of a treatment as defined in the first aspect of the invention and as described in any of the embodiments of the first aspect of the invention, wherein said treatment is non-therapeutic. Therefore, as understood by a skilled person, the treatment of the second aspect of the invention applied to a male subject is as that described in the first aspect of the invention, wherein no disease or disorder is being treated, or is to be treated, in the male subject with said treatment, such as infertility or any semen disorder.

In a certain embodiment, the number and/or concentration of spermatozoa in a semen sample of the male subject of the method of the invention, obtained after the treatment referred in said method, is higher than in a sample of semen of said male subject obtained before said treatment.

In a preferred embodiment, the number and/or the concentration of spermatozoa in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is higher than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the percentage of progressive motile spermatozoa in a sample of semen of the male subject of the method of the invention, obtained after the treatment referred in said method, is higher than in a sample of semen of said male subject obtained before said treatment.

In a preferred embodiment, the percentage of progressive motile spermatozoa in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is higher than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the percentage of morphologically normal spermatozoa in a sample of semen of the male subject of the method of the invention, obtained after the treatment referred in said method, is higher than in a sample of semen of said male subject obtained before said treatment.

In a preferred embodiment, the percentage of morphologically normal spermatozoa in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is higher than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the volume of semen per ejaculate in a semen sample of the male subject of the method of the invention, obtained after the treatment referred in said method, is higher than in a sample of semen of said male subject obtained before said treatment.

In a preferred embodiment, the volume of semen per ejaculate in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is higher than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the percentage of SDF in a sample of semen of the male subject of the method of the invention, obtained after the treatment referred in said method, is lower than in a sample of semen of said male subject obtained before said treatment.

In a preferred embodiment, the percentage of SDF in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is lower than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the level of 8-OH-dG in a sample of semen of the male subject of the method of the invention, obtained after the treatment referred in said method, is lower than in a sample of semen of said male subject obtained before said treatment.

In a preferred embodiment, the level of 8-OH-dG in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is lower than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the ratio 8-OH-dG/$10^5$ dG in a sample of semen of the male subject of the method of the invention, obtained after the treatment referred in said method, is lower than in a sample of semen of said male subject obtained before said treatment.

In a preferred embodiment, the ratio 8-OH-dG/$10^5$ dG in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is lower than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the percentage of 8-OH-dG positive sperm cells in a sample of semen of the male subject of the method of the invention, obtained after the treatment referred in said method, is lower than in a sample of semen of said male subject obtained before said treatment.

In a preferred embodiment, the percentage of 8-OH-dG positive sperm cells in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is lower than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the sORP in a sample of semen of the male subject of the method of the invention, obtained after the treatment referred in said method, is lower than in a sample of semen of said male subject obtained before said treatment.

In a preferred embodiment, the sORP in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is lower than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the concentration of leukocytes in a semen sample of the male subject of the method of the invention, obtained after the treatment referred in said method, is lower than in a sample of semen of said male subject obtained before said treatment.

In a preferred embodiment, the concentration of leukocytes in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is lower than in at least 1, at least 2, at least 3, at least 4, at least 5, at least 6, at least 7, at least 8, at least 9, at least 10, preferably than in at least 2 samples of semen of said male subject obtained before said treatment.

In a certain embodiment, the percentage of live spermatozoa in a semen sample of the male subject of the method of the invention, obtained after the treatment referred in said method, is higher than in a sample of semen of said male subject obtained before said treatment.

In a preferred embodiment, the percentage of live spermatozoa in at least 1, at least 2, at least 3, at least 4, at least 5, at least 6, at least 7, at least 8, at least 9, at least 10, preferably in at least 2 semen samples of the male subject of the method of the invention, obtained after the treatment referred in said method, is higher than in at least 1, at least 2, at least 3, at least 4, at least 5, at least 6, at least 7, at least 8, at least 9, at least 10, preferably than in at least 2 samples of semen of said male subject obtained before said treatment.

In certain embodiment, the expression "is higher than in a sample of semen of said male subject obtained before said treatment" when referring to the parameter "the number of spermatozoa", "the concentration of spermatozoa", "the percentage of progressive motile spermatozoa", "the percentage of morphologically normal spermatozoa", "the volume of semen per ejaculate", "the percentage of live spermatozoa" in a semen sample obtained after the treatment referred in the method of the invention, is understood as that the value of the corresponding parameter in the latest semen sample is at least 10%, at least 25%, at least 40%, at least 50%, at least 80%, at least 100%, at least 150%, at least 200%, at least 300%, at least 400%, at least 500%, at least 600%, at least 800%, or at least 1000%, preferably at least 25%, more preferably at least 50%, even more preferably at least 100%, yet more preferably at least 150% higher than the value of said parameter in the sample/s of semen obtained before the treatment.

In certain embodiment, the expression "is lower than in a sample of semen of said male subject obtained before said treatment" when referring to the parameter "the percentage of SDF", "the level of 8-OH-dG", "the ratio 8-OH-dG/$10^5$ dG", "percentage of 8-OH-dG positive sperm cells", "the sORP" and "the concentration of leukocytes" in a semen sample obtained after the treatment referred in the method of the invention, is understood as that the value of the corresponding parameter in the latest semen sample is at least 5%, at least 10%, at least 25%, at least 40%, at least 50%, at least 80%, at least 100%, preferably at least 25%, more preferably at least 50%, even more preferably at least 100% lower than the value of said parameter in the semen sample/s obtained before said treatment.

In a certain embodiment, the sample obtained after the treatment referred in the method of the invention is obtained at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 1 day, at least 2 days, at least 3 days, at least 5 days, at least 6 days, at least 1 week, at least 2 weeks, at least 3 weeks, at least 1 month, at least 2 months, at least 3 months, at least 6 months, at least 9 months, at least 1 year, at least 2 years, at least 3 years, at least 4 years, at least 5 years, after said treatment. In a further preferred embodiment, the sample obtained after the treatment referred in the method of the invention is obtained at least 1 month, more preferably at least 1 week, even more preferably at least 1 day, yet more preferably at least 1 hour after said treatment.

In a certain embodiment, the samples obtained after the treatment referred in the method of the invention are obtained at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 1 day, at least 2 days, at least 3 days, at least 5 days, at least 6 days, at least 1 week, at least 2 weeks, at least 3 weeks, at least 1 month, at least 2 months, at least 3 months, at least 6 months, at least 9 months, at least 1 year, at least 2 years, at least 3 years, at least 4 years, at least 5 years, after said treatment. In a further preferred embodiment, the samples obtained after the treatment referred in the method of the invention are obtained at least 1 month, more preferably at least 1 week, even more preferably at least 1 day, yet more preferably at least 1 hour after said treatment.

In a certain embodiment, the sample obtained before the treatment referred in the method of the invention is obtained at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 1 day, at least 2 days, at least 3 days, at least 5 days, at least 6 days, at least 1 week, at least 2 weeks, at least 3 weeks, at least 1 month, at least 2 months, at least 3 months, at least 6 months, at least 9 months, at least 1 year, at least 2 years, at least 3 years, at least 4 years, at least 5 years, before said treatment. In a further preferred embodiment, the sample obtained before the treatment referred in the method of the invention is obtained at least 1 month, more preferably at least 1 week, even more preferably at least 1 day, yet more preferably at least 1 hour before said treatment.

In a certain embodiment, the samples obtained before the treatment referred in the method of the invention are obtained at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 18 hours, at least 1 day, at least 2 days, at least 3 days, at least 5 days, at least 6 days, at least 1 week, at least 2 weeks, at least 3 weeks, at least 1 month, at least 2 months, at least 3 months, at least 6 months, at least 9 months, at least 1 year, at least 2 years, at least 3 years, at least 4 years, at least 5 years, before said treatment. In a further preferred embodiment, the samples obtained before the treatment referred in the method of the invention are obtained at least 1 month, more preferably at least 1 week, even more preferably at least 1 day, yet more preferably at least 1 hour before said treatment.

In a particular embodiment, the biomass of *T. chuii* referred in the method of the invention is dehydrated. In another particular embodiment, the biomass of *T. chuii* referred in the method of the invention is fresh.

The definitions of "fresh biomass of *T. chuii*", and "dehydrated biomass of *T. chuii*" have been provided in the first aspect of the invention and apply to the second aspect of the invention.

As indicated above, the treatment referred in the method of the invention is as the treatment of the first aspect of the invention, although it is non-therapeutic, and the embodiments provided in the first aspect of the invention in connection with the treatment of the first aspect of the invention apply to the treatment of the second aspect of the invention, with the proviso that said treatment is non-therapeutic. Thus, in a particular embodiment, the treatment referred in the method of the invention comprises administering 10-500 mg per day, preferably 250 mg per day of dehydrated biomass. In another particular embodiment, it comprises administering 30 mg-4 g of fresh biomass per day, preferably 4 g, more preferably 3 g, even more preferably 40 mg, yet more preferably 30 mg of fresh biomass per day. In another particular embodiment, it comprises administering 4-200 mg of protein extract per day, preferably 100 mg of protein extract of *T. chuii* per day.

In another preferred embodiment, the treatment referred in the second aspect of the invention comprises the administration of the biomass, or the protein extract as defined herein, for at least 30 days (i.e. 1 month). In another preferred embodiment, the treatment referred in the second aspect of the invention comprises the administration of the biomass, or the protein extract as defined herein for at least 65 days. In another preferred embodiment the treatment referred in the second aspect of the invention comprises the administration of the biomass, or the protein extract as defined herein for at least 70 days. In another preferred embodiment the treatment referred in the second aspect of the invention comprises the administration of the biomass, or the protein extract as defined herein for at least 90 days.

All the terms and embodiments described in the first aspect of the invention are equally applicable to this aspect of the invention.

III—Use of the Invention

In a third aspect, the invention relates to a use of a biomass of *T. chuii* or a protein extract of *T. chuii* as an oral supplement for increasing the quality of the semen of a male subject having normozoospermia, not having hypospermia, and not having a disorder characterized by a percentage of SDF in a semen sample above a reference value. In another particular embodiment, the subject of the third aspect of the invention does not have a disorder characterized by a level of 8-OH-dG, a ratio 8-OH-dG/$10^5$ dG, or a percentage of 8-OH-dG positive sperm cells, in semen above a reference value. In another particular embodiment, the subject of the third aspect of the invention does not have a disorder characterized by a sORP in semen above a reference value. In a particular embodiment, the subject of the third aspect of the invention does not have aspermia. In a particular embodiment, the subject of the third aspect of the invention does not have leukospermia. In another particular embodiment, the subject of the third aspect of the invention does not have necrozoospermia. In another particular embodiment, the subject of the third aspect of the invention has normozoospermia, does not have hypospermia, does not have a disorder characterized by a percentage of SDF in a semen sample above a reference value, does not have a disorder characterized by a level of 8-OH-dG, a ratio 8-OH-dG/$10^5$ dG, or a percentage of 8-OH-dG positive sperm cells, in semen above a reference value, does not have a disorder characterized by a level of sORP in semen above a reference value, does not have aspermia, does not have leukospermia and does not have necrozoospermia.

The expression "oral supplement" as used herein, refers to any product that is provided together with the diet of a subject and that is administered orally. An oral supplement can take very different forms, including tablets, capsules, liquid suspensions, dried powder, wet composition, a dry tube feeding or a wet tube feeding. In a preferred embodiment, the oral supplement comprises, or consists of, the biomass of *T. chuii*, the protein extract of *T. chuii* or the pharmaceutical composition as defined and described in any embodiment in the first aspect of the invention. In another preferred embodiment, the oral supplement, the biomass of *T. chuii* or the protein extract of *T. chuii* referred in the use of the invention, is administered as indicated in any embodiment of first aspect of the invention for the administration of the biomass of *T. chuii*, the protein extract of *T. chuii* or the pharmaceutical composition comprised within the treatment referred in the first aspect of the invention. Thus, in a particular embodiment, the oral supplement, the biomass of *T. chuii* or the protein extract of *T. chuii* referred in the use of the invention, is administered for the period of time, the frequency and the dose indicated in any embodiment of the first aspect of the invention specifying the period of time, the frequency and the dose of administration of the biomass, protein extract or pharmaceutical composition referred in the first aspect of the invention.

The expressions "quality of the semen of a male subject", and "increasing the quality of the semen of a male subject" are as defined and described in any embodiment in the second aspect of the invention.

The definition of the terms "normozoospermia", "hypospermia", "percentage of SDF", "aspermia", "leukospermia", "necrozoospermia", "level of 8-OH-dG in semen", "ratio 8-OH-dG/$10^5$ dG in semen", "percentage of 8-OH-dG positive sperm cells" and "level of sORP in semen" have also been provided in the first or second aspect of the invention and applies to this aspect of the invention.

The expression "a percentage of SDF above a reference value" is as defined and described in any embodiment of the first and second aspect of the invention.

In a preferred embodiment, the reference value of the percentage of SDF is any of those indicated in the first aspect of the invention.

The expression "a level of 8-OH-dG in semen above a reference value" is as defined and described in any embodiment of the first and second aspect of the invention.

In a preferred embodiment, the reference value of the level of 8-OH-dG in semen is any of those indicated in the first aspect of the invention.

The expression "a ratio 8-OH-dG/$10^5$ dG in semen above a reference value" is as defined and described in any embodiment of the first and second aspect of the invention.

In a preferred embodiment, the reference value of the ratio 8-OH-dG/$10^5$ dG in semen is any of those indicated in the first aspect of the invention.

The expression "a percentage of 8-OH-dG positive sperm cells in semen above a reference value" is as defined and described in any embodiment of the first and second aspect of the invention.

In a preferred embodiment, the reference value of the percentage of 8-OH-dG positive sperm cells in semen is any of those indicated in the first aspect of the invention.

The expression "a sORP in semen above a reference value" is as defined and described in any embodiment of the first and second aspect of the invention.

In a preferred embodiment, the reference value of the sORP in semen is any of those indicated in the first aspect of the invention.

In a particular embodiment, the male subject of the third aspect of the invention is as the male subject of the second aspect of the invention. In a preferred embodiment, the male subject of the third aspect of the invention is fertile.

The expression "fertile" is as defined and described in any of the embodiments of the second aspect of the invention.

In a certain embodiment, all the terms and embodiments described in the first and second aspect of the invention are equally applicable to this aspect of the invention.

In a certain embodiment, the terms "comprising" and "consisting of" used in the first, second and third aspects of the invention are interchangeable.

The invention will be described by way of the following examples which are to be considered as merely illustrative and not limitative of the scope of the invention.

EXAMPLES

Materials and Methods

A total of 20 individuals exhibiting idiopathic oligozoospermia, asthenozoospermia, and/or teratozoospermia (according to a first complete semen analysis) were recruited. Each of these states was defined according to the World Health Organization (WHO) parameters, described in the "WHO laboratory manual for the Examination and processing of human semen" (Fifth Edition, 2010). More specifically, the nomenclature oligozoospermia refers to a total number (or concentration, depending on the outcome reported) of spermatozoa below the lower reference limit (LRL), $39 \times 10^6$ sperm per ejaculate (or $15 \times 10^6$ sperm/ml if concentration is reported). Regarding asthenozoospermia, it occurs when the percentage of progressive motile (PR) spermatozoa is below the LRL (32%). Finally, teratozoospermia is diagnosed when the percentage of morphologically normal spermatozoa is below the LRL (4%). In relation to this nomenclature, PR refers to spermatozoa moving actively, either linearly or in a large circle, regardless of speed; and for a spermatozoon to be considered morphologically normal: i) Head: it should be smooth, regularly contoured and generally oval in shape. There should be a well-defined acrosomal region comprising 40-70% of the head area. The acrosomal region should contain no large vacuoles, and not more than two small vacuoles, which should not occupy more than 20% of the sperm head. The post-acrosomal region should not contain any vacuoles; ii) Midpiece: it should be slender, regular and about the same length as the sperm head. The major axis of the midpiece should be aligned with the major axis of the sperm head. Residual cytoplasm is considered an anomaly only when in excess, i.e. when it exceeds one third of the sperm head size; iii) Principal piece: it should have a uniform calibre along its length, be thinner than the midpiece, and be approximately 45 μm long (about 10 times the head length). It may be looped back on itself, provided there is no sharp angle indicative of a flagellar break.

Semen samples were collected just before the commencement of the treatment (t=0), and after 3 months of treatment (t=3 months) with dietary supplementation with *Tetraselmis chuii* (250 mg/day), following the standard procedure described by the WHO (2010). Several parameters were quantified in those samples at both sampling times: i) Semen volume (VOL; ml), ii) Sperm concentration (CONC; $10^6$ per ml), iii) Total sperm number (NUM; $10^6$ per ejaculate), iv) PR (%), and v) Sperm morphology (MORF; normal forms, %). All these parameters were determined following the guidelines and protocols provided by the WHO (2010).
Statistical Analysis First of all, descriptive statistics (mean and SEM) were determined for each parameter. Then, the non-parametric Wilcoxon test for matched-pairs was applied in order to determine statistically significant differences of data recorded before and after *T. chuii* supplementation. Significance was accepted for $p<0.05$. All analyses were conducted with Prism 6 software.
Results

Example 1

Semen Volume (VOL)

As shown in FIG. 1, a highly statistically significant increase in VOL was observed after three months of supplementation with *T. chuii*. The parameter VOL reached a mean value of 3.09 ml, representing a close to 35% increase in relation to the mean value observed at the commencement of the trial (2.29 ml).

Figure 2:
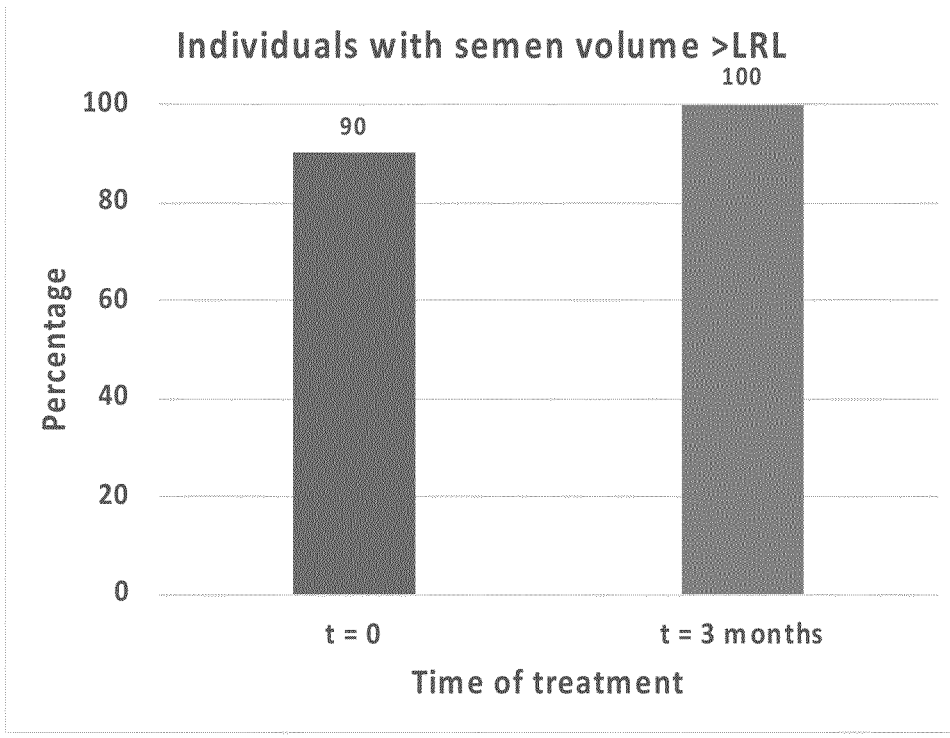
FIG. 2 shows the percentage of participants in the trial presenting values for the parameter VOL higher than the LRL stablished by the WHO ("WHO laboratory manual for the Examination and processing of human semen", 2010, fifth edition) both at the commencement of the trial and after 3 months of *T. chuii* supplementation.

When participants in the trial were classified with regard to the LRL established by the WHO for this parameter (FIG. 2), it was found that 90% of them presented values higher than the LRL at t=0, but after the trial completion, all values recorded (100%) were higher than the LRL.

Example 2

Sperm Concentration (CONC)

Figure 3:
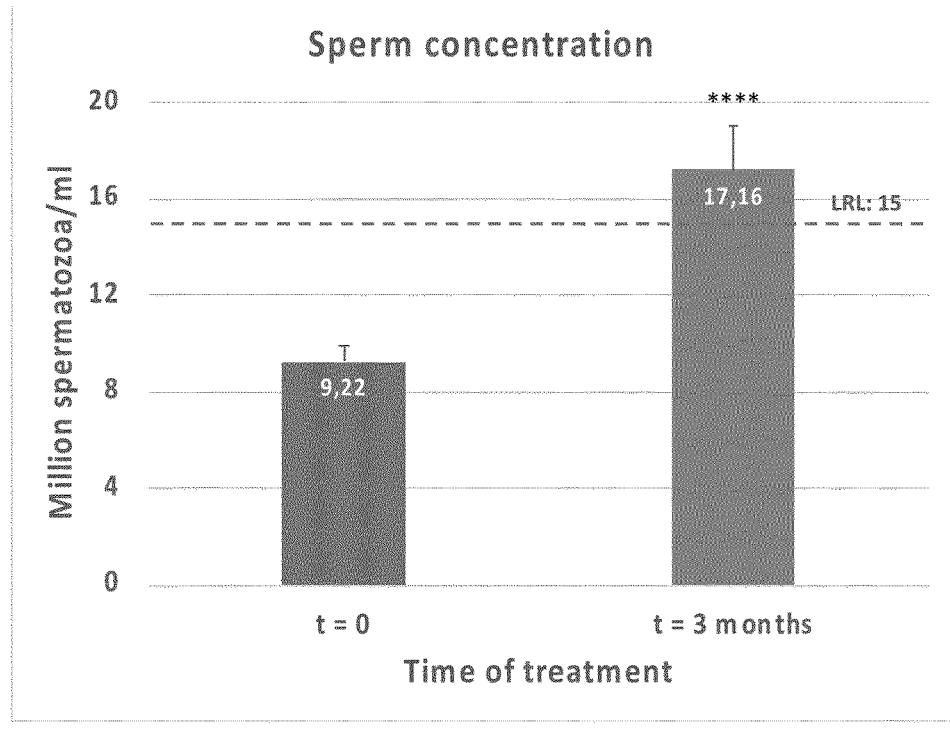
FIG. 3 shows mean values (+SEM) of the parameter sperm concentration (CONC) just at the commencement of the trial and after 3 months of supplementation with *T. chuii*. The dashed line indicates the LRL stablished by the WHO ("WHO laboratory manual for the Examination and processing of human semen", 2010, fifth edition). ****: $p<0.0001$.
Figure 4:
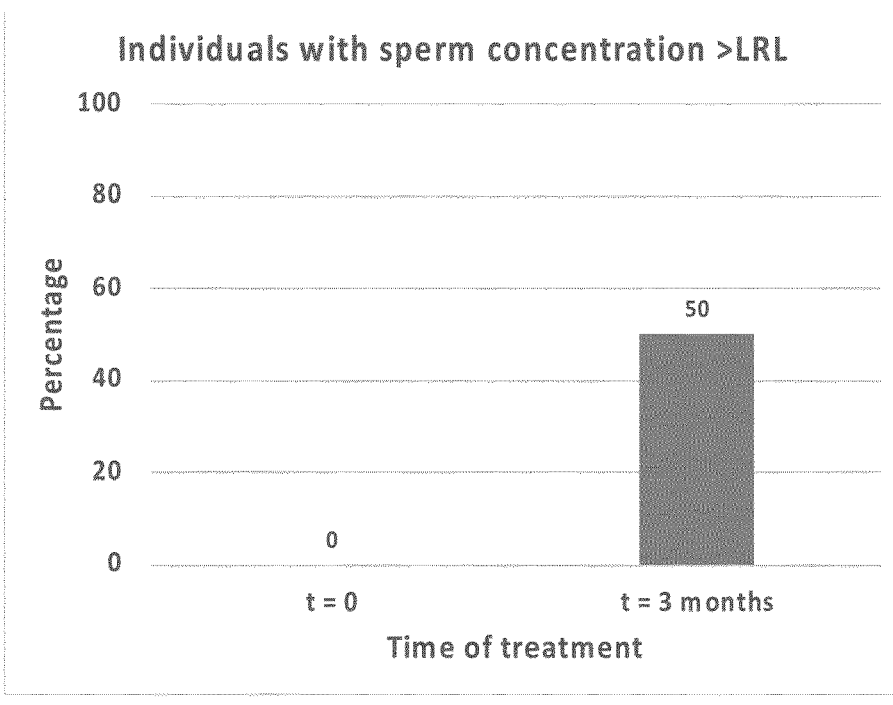
FIG. 4 shows the percentage of participants in the trial presenting values for the parameter CONC higher than the LRL stablished by the WHO ("WHO laboratory manual for the Examination and processing of human semen", 2010, fifth edition) both at the commencement of the trial and after 3 months of *T. chuii* supplementation.

A highly statistically significant increase in the parameter CONC was also observed after three months of supplementation with *T. chuii* (FIG. 3). Actually, the mean value was $17.16 \times 10^6$ sperm/ml, representing a ~86% increase in relation to the initial mean value recorded at t=0 ($9.22 \times 10^6$ sperm/ml). Importantly, such mean value after 3 months of dietary supplementation with *T. chuii* was higher (14.4%) than the LRL established by the WHO ($15 \times 10^6$ sperm/ml).

In this case, the effects of *T. chuii* supplementation were dramatically positive when looking at individual classification according to the LRL provided by the WHO. No participants exhibited a value >LRL at t=0, that is, 100% presented oligozoospermia, but this percentage dropped to 50% after 3 months of *T. chuii* intake.

Example 3

Total Sperm Number in Ejaculate (NUM)

Figure 5:
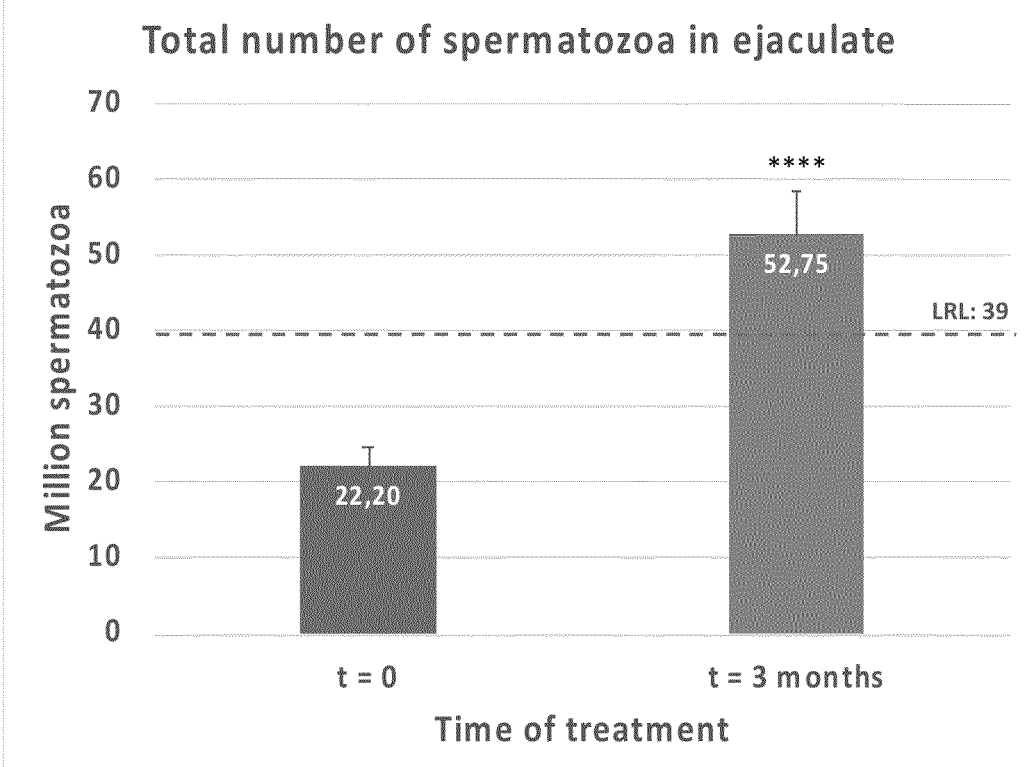
FIG. 5 shows mean values (+SEM) of the parameter number of spermatozoa per ejaculate (NUM) just at the commencement of the trial and after 3 months of supplementation with *T. chuii*. The dashed line indicates the LRL stablished by the WHO ("WHO laboratory manual for the Examination and processing of human semen", 2010, fifth edition). ****: p<0.0001.

FIG. 5 summarizes the results obtained in the trial. A strongly significant increase in NUM was detected as a consequence of *T. chuii* supplementation. While at t=0 the mean value was $22.20 \times 10^6$ sperm per ejaculate, after 3 months of daily *T. chuii* intake the recorded mean value was $52.75 \times 10^6$ sperm per ejaculate, representing a ~238% increase in relation to initial value. Moreover, with regard to the LRL proposed by the WHO for this parameter, the observed change was dramatic: at t=0 the mean value was significantly lower than the LRL (represented only 57% of this reference value), whereas after 3 months of *T. chuii* consumption the mean value was ~35% higher than that LRL.

Figure 6:
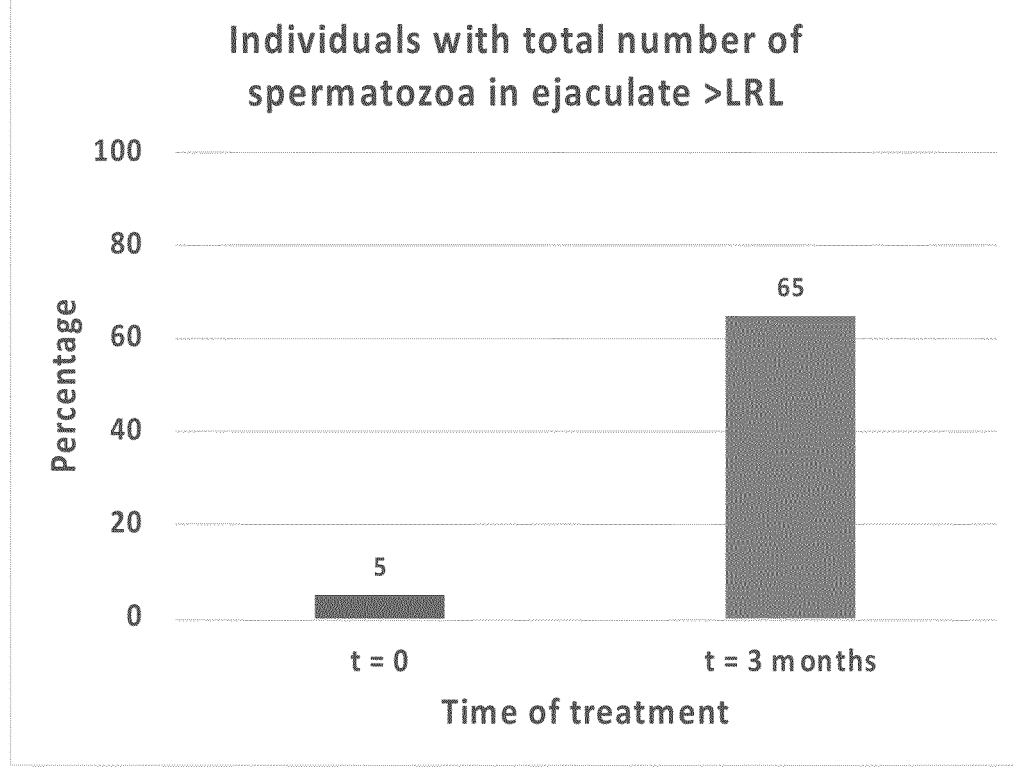
FIG. 6 shows the percentage of participants in the trial presenting values for the parameter NUM higher than the LRL stablished by the WHO ("WHO laboratory manual for the Examination and processing of human semen", 2010, fifth edition) both at the commencement of the trial and after 3 months of *T. chuii* supplementation.

Impressive results were again observed regarding the distribution of participants in the trial according to the LRL established by the WHO for the parameter NUM. As shown in FIG. 6, only 1 individual (5%) exhibited a value for NUM>LRL, that is, 95% of them (19 out of 20) presented oligozoospermia. But after *T. chuii* consumption during 3 months, the percentage of participants with oligozoospermia decreased to 35%.

Example 4

Progressive Motility (PR)

Figure 7:
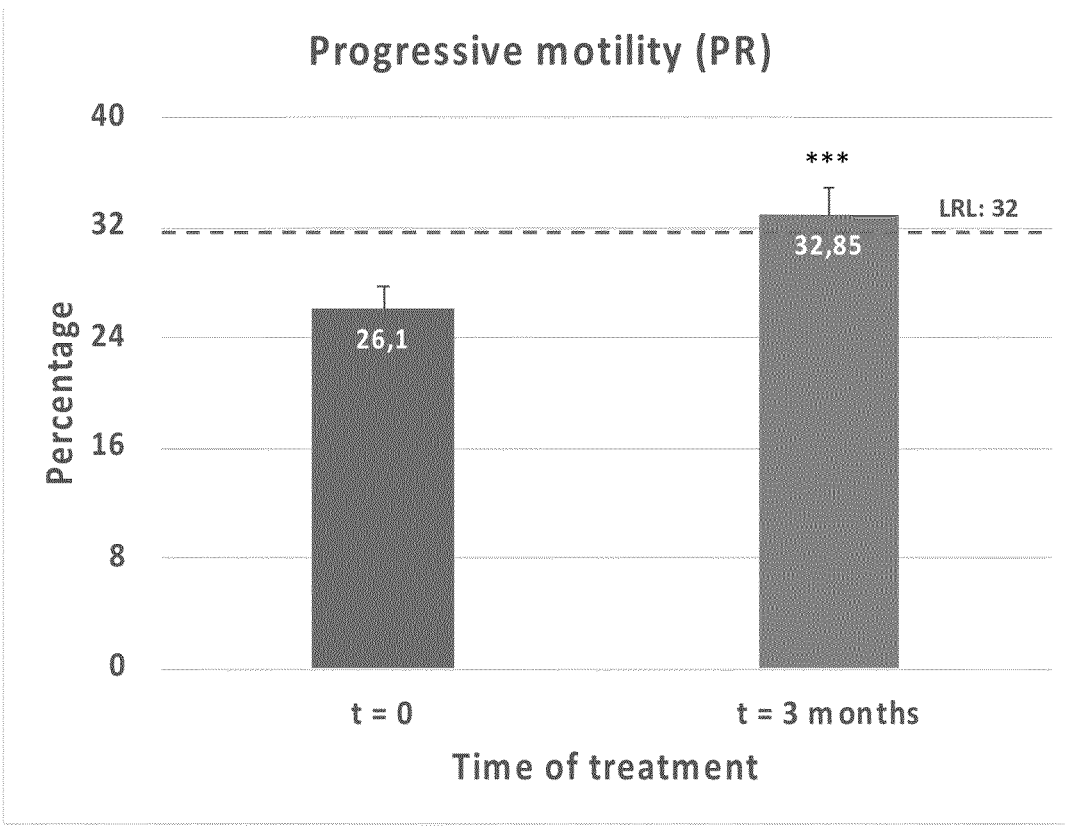
FIG. 7 shows mean values (+SEM) of the parameter Progressive motility (PR) just at the commencement of the trial and after 3 months of supplementation with *T. chuii*. The dashed line indicates the LRL stablished by the WHO ("WHO laboratory manual for the Examination and processing of human semen", 2010, fifth edition). ***: p<0.001.

As observed with previous parameters, a statistically significant increase was detected also in PR after *T. chuii* consumption during 3 months (FIG. 7). The average mean value changed from 26.1% at the commencement of the trial to 32.85% at the end, representing a net 25.9% increase in this parameter. In addition, it has to be highlighted that the final mean value after 3 months of *T. chuii* supplementation was even slightly higher that the LRL provided by the WHO for PR (32%).

Figure 8:
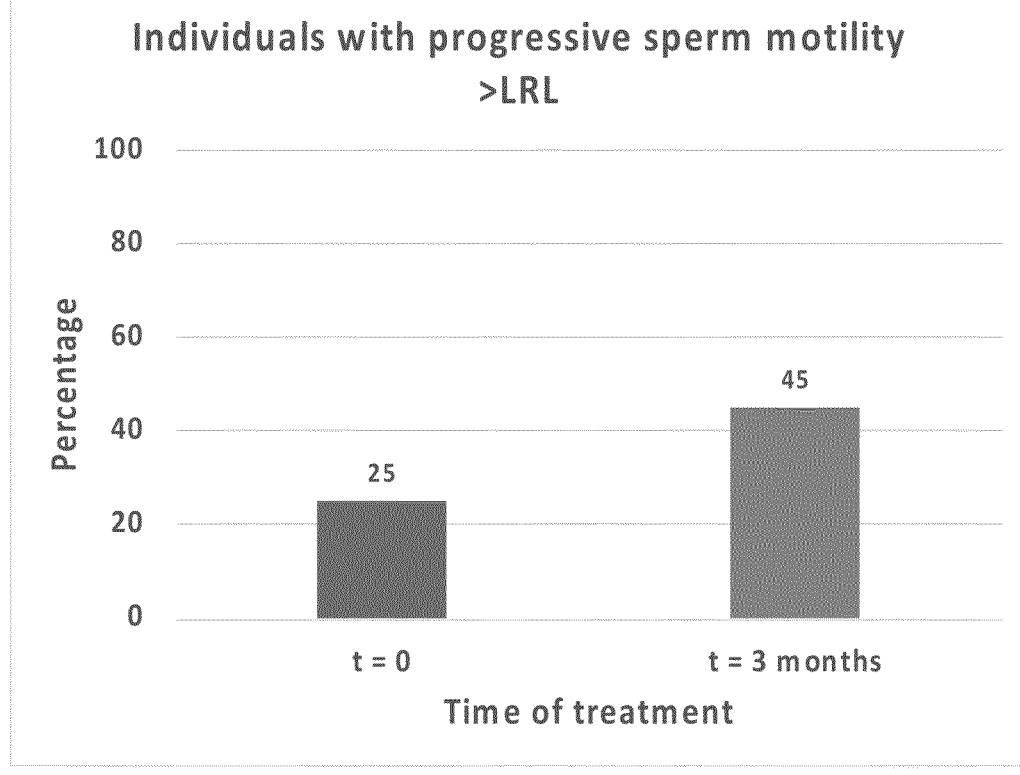
FIG. 8 shows the percentage of participants in the trial presenting values for the parameter PR higher than the LRL stablished by the WHO ("WHO laboratory manual for the Examination and processing of human semen", 2010, fifth edition) both at the commencement of the trial and after 3 months of *T. chuii* supplementation.

When dealing with classification of participants in relation to the LRL provided by the WHO for PR (FIG. 8), 75% of them presented asthenozoospermia at t=0 (as only 25% exhibited a value >LRL), but this percentage decreased to 55% as a consequence of *T. chuii* supplementation for 3 months (45% of participants with a value >LRL).

Example 5

Normal Forms (MORF)

Figure 9:
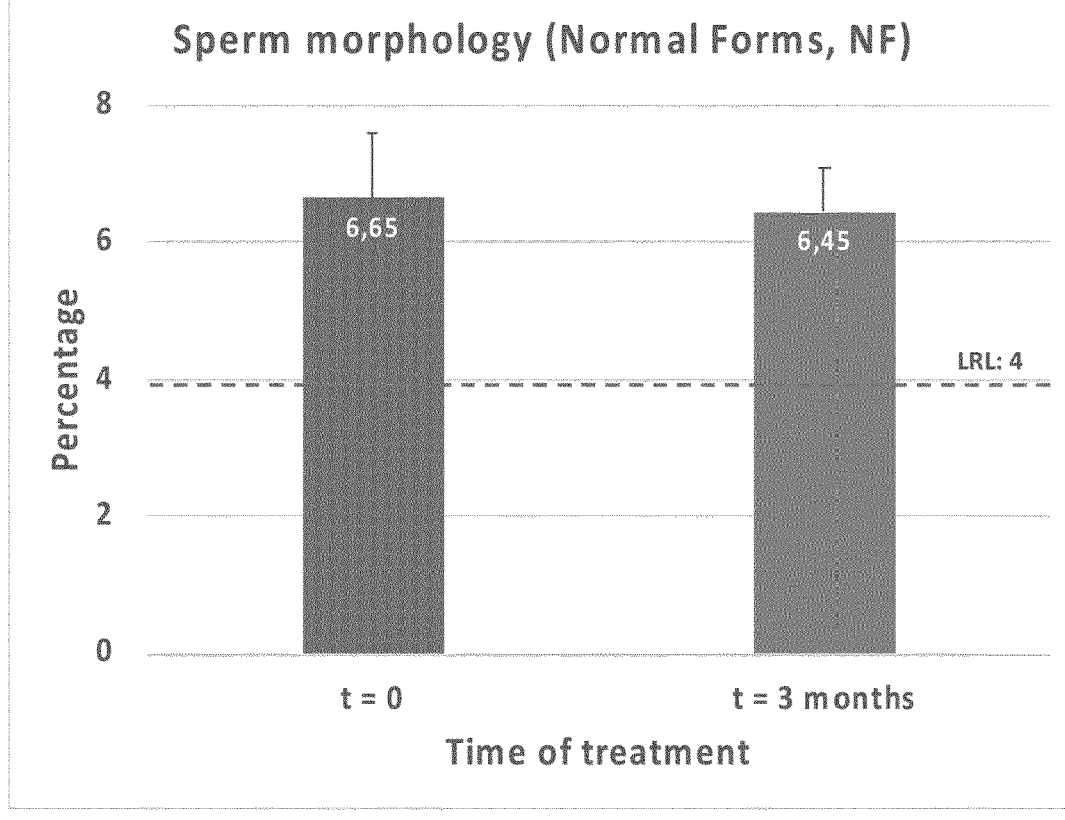
FIG. 9 shows mean values (+SEM) of the parameter normal morphology (MORF) just at the commencement of the trial and after 3 months of supplementation with *T. chuii*. The dashed line indicates the LRL stablished by the WHO ("WHO laboratory manual for the Examination and processing of human semen", 2010, fifth edition).

As presented in FIG. 9, in contrast to all previous parameters already described, no statistically significant changes were detected in the mean values recorded both at the commencement (6.65%) and at the end (6.45%) of the trial. Moreover, both mean values were higher than the LRL provided by the WHO (4%) for this parameter.

Figure 10:
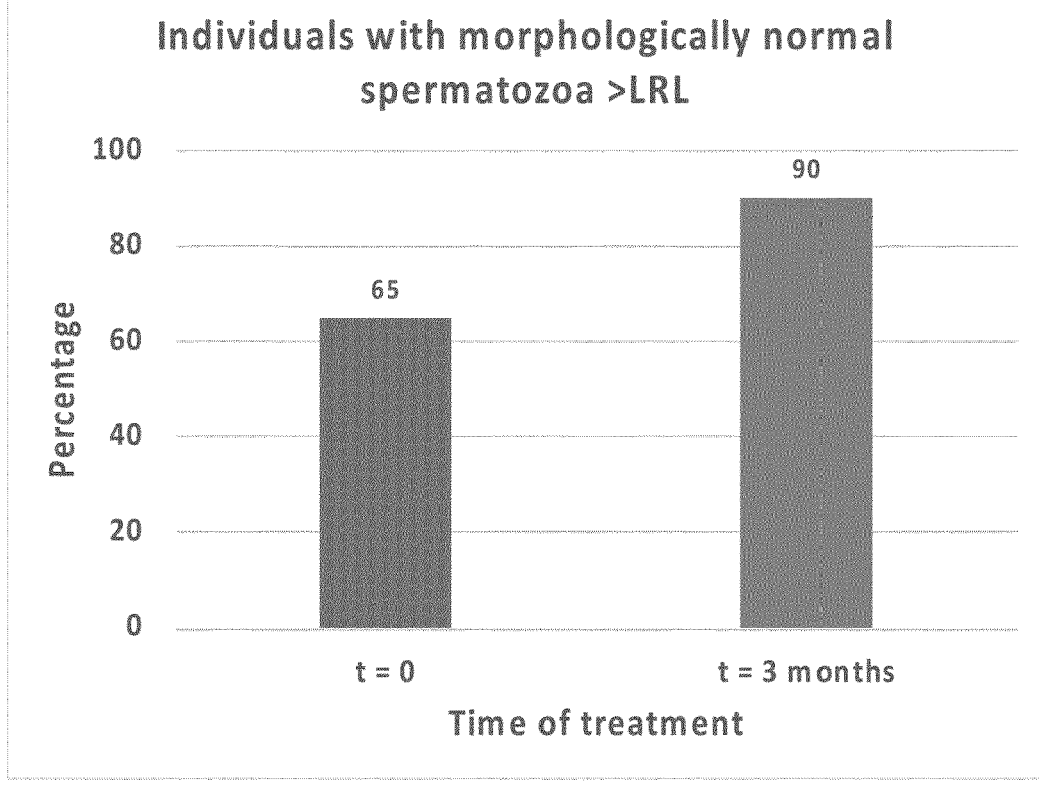
FIG. 10 shows the percentage of participants in the trial presenting values for the parameter MORF higher than the LRL stablished by the WHO ("WHO laboratory manual for the Examination and processing of human semen", 2010, fifth edition) both at the commencement of the trial and after 3 months of *T. chuii* supplementation.

However, when we looked at distribution of participants in relation to the LRL, we observed that 35% presented teratozoospermia at t=0 (that is, 65% exhibited a value >LRL), but this percentage of individuals with teratozoospermia dropped to 10% (90% of individuals exhibiting a value >LRL) at the end of the trial (FIG. 10).

Example 6

Normozoospermia

Figure 11:
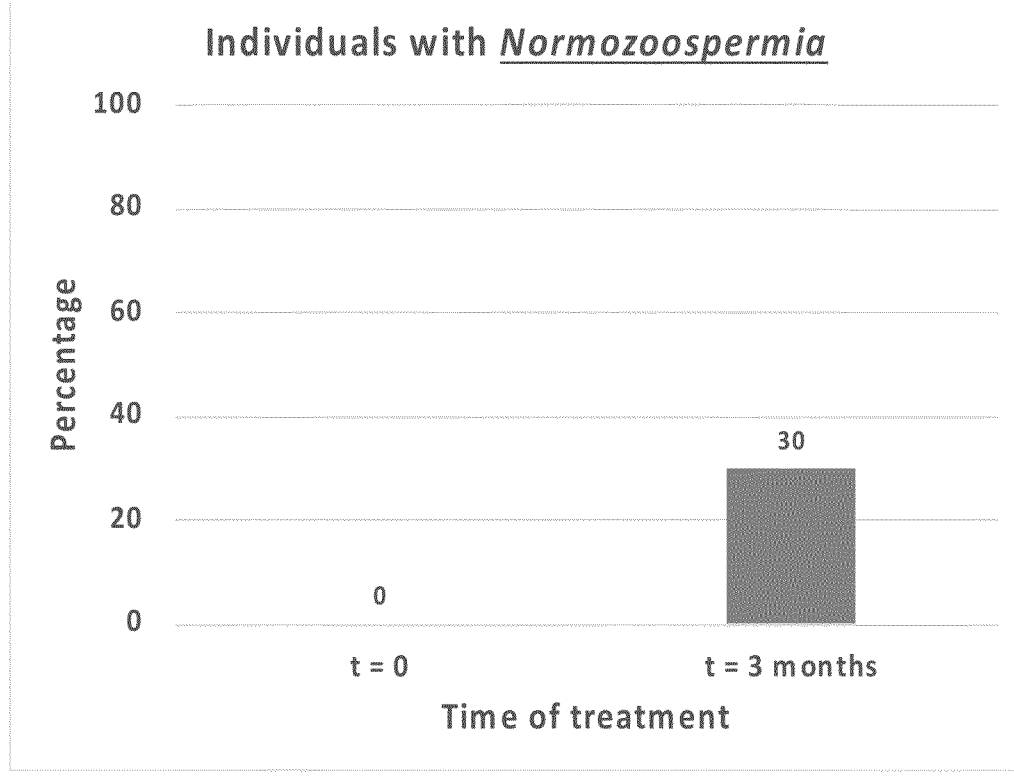
FIG. 11 shows the percentage of participants in the trial with normozoospermia (according to the criteria provided by the WHO in "WHO laboratory manual for the Examination and processing of human semen", 2010, fifth edition) both at the commencement of the trial and after 3 months of *T. chuii* supplementation.

According to the WHO (2010), an individual with normozoospermia has a total number (or concentration, depending on outcome reported) of spermatozoa, and percentages of progressively motile (PR) and morphologically normal spermatozoa (NF), equal to or above the LRLs. Thus, this status of normozoospermia reveals as relevant for analysis as it englobes important parameters of semen quality. As shown in FIG. 11, no individuals included in the trial presented normozoospermia at t=0 (as described in Introduction, individuals were included in the study as they exhibited oligozoospermia, asthenozoospermia, and/or teratozoospermia). But after 3 months of *T. chuii* consumption, percentage of participants with normozoospermia increased to 30% (6 out of 20 individuals).

CONCLUSIONS

All data considered, results obtained with supplementation of *T. chuii* (250 mg/day during 3 months) revealed a statistically significant positive response in the mean value of 4 out of 5 parameters analyzed in semen samples. When dealing with percentages of individuals classified according to LRLs (provided by the WHO, 2010) in each of those parameters, a positive result was obtained in all cases. Thus, administration the microalgae *T. chuii* improves semen quality in infertile men having abnormal semen parameters.

The invention claimed is:

1. A method for treating infertility in a male patient, comprising administering a biomass of *Tetraselmis chuii* (*T. chuii*) or a pharmaceutical composition comprising the biomass of *T. chuii* to said patient.

2. The method according to claim 1, wherein the patient has oligozoospermia or azoospermia.

3. The method according to claim 1, wherein the patient has asthenozoospermia.

4. The method according to claim 1, wherein the patient has teratozoospermia.

5. The method according to claim 1, wherein the patient has hypospermia or aspermia.

6. The method according to claim 1, wherein the patient has a disorder characterized by a percentage of sperm DNA fragmentation (SDF) above a reference value.

7. The method according to claim 1, wherein the patient has a disorder characterized by a level of 8-hydroxy,2-deoxyguanosine (8-OHdG), a ratio $8\text{-OH-dG}/10^5$ dG or a percentage of 8-OH-dG positive sperm cells, in semen above a reference value.

8. The method according to claim 1, wherein the patient has a disorder characterized by a level of static Oxidation-reduction Potential (sORP) in semen above a reference value.

9. The method according to claim 1, wherein the male patient has leukospermia.

10. The method according to claim 1, wherein the biomass of *T. chuii* is dehydrated.

11. The method according to claim 1, wherein the treatment comprises administering 10-500 mg/day of dehydrated biomass.

12. The method according to claim 1, wherein the treatment comprises administering the biomass or the pharmaceutical composition for at least 1 month.

13. The method according to claim 1, wherein the treatment comprises administering 250 mg/day of dehydrated biomass.

* * * * *